(12) United States Patent
Scales et al.

(10) Patent No.: US 7,718,432 B2
(45) Date of Patent: May 18, 2010

(54) NON-IMMUNOGENIC, HYDROPHILIC/CATIONIC BLOCK COPOLYMERS AND USES THEREOF

(75) Inventors: Charles W. Scales, San Ramon, CA (US); Faqing Huang, Hattiesburg, MS (US); Charles L. McCormick, Hattiesburg, MS (US)

(73) Assignee: The University of Southern Mississippi, Hattiesburg, MS (US)

( * ) Notice: Subject to any disclaimer, the term of this patent is extended or adjusted under 35 U.S.C. 154(b) by 314 days.

(21) Appl. No.: 11/725,964

(22) Filed: Mar. 20, 2007

(65) Prior Publication Data

US 2007/0259828 A1 Nov. 8, 2007

Related U.S. Application Data

(60) Provisional application No. 60/784,803, filed on Mar. 22, 2006.

(51) Int. Cl.
*C12N 15/63* (2006.01)
*C12Q 1/68* (2006.01)
*C07H 21/04* (2006.01)
*C08F 2/00* (2006.01)

(52) U.S. Cl. ............... 435/455; 435/6; 524/555; 526/217; 526/220; 526/222; 526/225; 536/23.1; 536/24.5

(58) Field of Classification Search ............ 435/6, 435/91.1, 458, 455; 424/1.21, 1.29; 526/222, 526/217, 225, 220; 524/555; 536/23.1, 24, 536/5

See application file for complete search history.

(56) References Cited

U.S. PATENT DOCUMENTS 7,186,786 B2 3/2007 McCormick et al. ........ 526/222

FOREIGN PATENT DOCUMENTS

WO WO 98/01478 1/1998

OTHER PUBLICATIONS

Lorenzo et al., Languir, vol. 21, pp. 5142-5148 (2005).*
Kabanov et al., Advanced Drug Delivery Rev., vol. 30, pp. 49-60 (1998).*
Wang, et al, (1999), Hybrid hydrogels assembled from synthetic polymers and coiled-coil protein domains, *Nature*, vol. 397, pp. 417-420.
Jensen, et al, (2003), Cytoplasmic delivery and nuclear targeting of synthetic macromolecules, *J. Control. Release*, vol. 87, pp. 89-105.
Andersson, et al, (2004), Complexation of DNA with poly(methacryl oxyethyl trimethylammonium chloride) and its poly(oxyethylene) grafted analogue, *Biomacromolecules*, vol. 5, pp. 1853-1861.
Alvarez-Lorenzo, et al, (2005), Biophysical characterization of complexation of DNA with block copolymers of poly(2-dimethylaminoethyl) methacrylate, poly(ethylene oxide), and poly(propylene oxide), *Langmuir*, vol. 21, pp. 5142-5148.
van de Wetering, et al, (1999), Comparative transfection studies of human ovarian carcinoma cells in vitro, ex vivo and in vivo with poly(2-(dimethylamino)ethyl methacrylate)-based polyplexes, *J. Gene Med.*, vol. 1, pp. 156-165.
Kabanov, et al, (1998), Interpolyelectrolyte and block ionomer complexes for gene delivery: physico-chemical aspects, *Adv. Drug Deliv. Rev.*, vol. 30, pp. 49-60.
Kabanov, et al, (1995), DNA complexes with polycations for the delivery of genetic material into cells, *Bioconjug. Chem.*, vol. 6, pp. 7-20.
Kopecek, et al, (2000), HPMA copolymer-anticancer drug conjugates: design, activity, and mechanism of action, *Eur. J. Pharm. Biopharm.*, vol. 50, pp. 61-81.
Vasey, et al, (1999), Phase I clinical and pharmacokinetic study of PK1 [N-(2-Hydroxypropyl)methacrylamide copolymer doxorubicin]: first member of a new class of chemotherapeutic agents—drug-polymer conjugates, *Clinical Cancer Research*, vol. 5, pp. 83-94.
Vasilieva, et al, (2004), Direct controlled polymerization of a cationic methacrylamido monomer in aqueous media via the RAFT process, *Macromolecules*, vol. 37, pp. 2728-2737.
Scales, et al, (2006), Corona-stabilized interpolyelectrolyte complexes of siRNA with nonimmunogenic, hydrophilic/cationic block copolymers prepared by aqueous RAFT polymerization, *Macromolecules*, vol. 39, pp. 6871-6881.

* cited by examiner

*Primary Examiner*—Jane Zara
(74) *Attorney, Agent, or Firm*—Howrey LLP

(57) ABSTRACT

The present invention provides novel non-immunogenic, hydrophilic/cationic block copolymers comprising a neutral-hydrophilic polymer and a cationic polymer, wherein both polymers have well-defined chain-end functionality. A representative example of such a block copolymer comprises poly (N-(2-hydroxypropyl)methacrylamide) (PHPMA) and poly (N-[3-(dimethylamino)propyl]methacrylamide) (PDMAPMA). Also provided is a synthesis method thereof in aqueous media via reversible addition fragmentation chain transfer (RAFT) polymerization. Further provided are uses of these block copolymers as drug delivery vehicles and protection agents.

15 Claims, 11 Drawing Sheets

NON-IMMUNOGENIC, HYDROPHILIC/CATIONIC BLOCK COPOLYMERS AND USES THEREOF

This application claims the benefit of priority to U.S. Provisional Application Ser. No. 60/784,803, filed Mar. 22, 2006, which is herein incorporated by reference in its entirety.

The United States government may own rights to the present invention pursuant to grant numbers DMR-0213883 from the MRSEC program of the National Science Foundation and DE-FC26-01BC15317 from the U.S. Department of Energy.

FIELD OF THE INVENTION

The present invention generally relates to polymer chemistry and drug delivery. In particular, the present invention relates to novel hydrophilic/cationic block copolymers comprising the non-immunogenic, hydrophilic poly(N-(2-hydroxypropyl)methacrylamide) (PHPMA) and the cationic poly(N-[3-(dimethylamino)propyl]methacrylamide) (PDMAPMA). The present invention also relates to synthesis of such hydrophilic/cationic block copolymers via aqueous reversible addition fragmentation chain transfer (RAFT) polymerization and uses of such copolymers in drug delivery.

BACKGROUND OF THE INVENTION

Poly(N-(2-hydroxypropyl)methacrylamide) (PHPMA) as a delivery vehicle has been well studied over the past few decades (Jensen et al., 2003; incorporated herein by reference). Originally, much of the work with this neutral, hydrophilic, biocompatible polymer focused on its use as a plasma expander; however, it has more recently been employed in the delivery of anticancer drugs (Kopecek et al., 2000; Putnam and Kopecek, 1995; Vasey et al., 1999; Duncan et al., 1992), site specific delivery in the GI tract (Yeh et al., 1995; Kopeckova et al., 1994), tumor-specific delivery of antisense oligonucleotides to their target mRNAs (Wang et al., 1999; Jensen et al., 2001), and hydrogels (Yeh et al., 1995; Wang et al., 1999; Subr et al., 1990; Rihova et al., 1997). As with other successful delivery vehicles, drug conjugates of PHPMA are well suited to pharmaceutical applications because they exhibit the enhanced permeability and retention (EPR) effect, therefore increasing the concentration of an active drug in tumor cells (i.e. 10-100 times higher concentration than that of the free drug) and decreasing the dose limiting toxicity (Matsumura and Maeda, 1986; Duncan, 1997).

Controlling the free-radical polymerization of N-(2-hydroxypropyl)methacrylamide (HPMA) and, therefore, controlling the molecular weight and molecular weight distribution of PHPMA is a crucial factor in the synthesis of well defined polymer-drug conjugates. The first attempts to control the polymerization of HPMA were reported by Teodorescu and Matyjaszewski (1999 and 2000) and employed atom transfer radical polymerization (ATRP) in organic media (1-butanol or ethanol) with two different ligand-initiating systems. However, these systems suffered from elevated polydispersities ($M_w/M_n$) and, in some cases, low conversions. An indirect method for the preparation of well-defined polymers of HPMA and PHPMA-drug conjugates was demonstrated by Godwin et al. (2001) in which N-methacryloxysuccinimide was first polymerized via ATRP followed by reaction of the succinimidyl-ester side-chains with stoichiometric amounts of 1-amino-2-propanol and an amino-terminal, peptide-linked "model drug," glycine-glycine-β-naphthylamide.

In recent years, efforts have been focused on the controlled polymerization of water-soluble, acrylamido monomers via reversible addition-fragmentation chain transfer (RAFT) polymerization (McCormick et al., 2004; incorporated herein by reference). To date, the controlled RAFT polymerization of anionic, zwitterionic, and neutral acrylamido monomers has been reported in both organic and aqueous media employing a variety of chain transfer agents (CTA) including xanthates, dithiocarbamates, trithiocarbonates and dithioesters. All of these CTAs can afford control over the molecular weight and yield (co)polymers with low $M_w/M_n$ values under appropriate conditions.

Most recently, attention has turned to methacrylamido monomers and the first "truly" controlled polymerization of HPMA via aqueous RAFT polymerization mediated by 4-cyanopentanoic acid dithiobenzoate (CTP) (Scales et al., 2005; incorporated herein by reference). HPMA was polymerized with good control over the molecular weight and polydispersity ($M_w/M_n$) in an acetic acid/sodium acetate buffer solution. The first RAFT polymerization of a cationic methacrylamido species, namely N-[3-(dimethylamino)propyl]methacrylamide (DMAPMA), mediated by CTP in aqueous media under the same conditions used for the polymerization of HPMA has also been reported (Vasilieva et al., 2004; incorporated herein by reference). DMAPMA was also polymerized in an acetic buffer with good control over the molecular weight ($M_n$=47,000 g/mol, $M_w/M_n$=1.08), while the corresponding polymerization in water alone exhibited a loss of control due to thiocarbonylthio hydrolysis ($M_n$=44,500 g/mol, $M_w/M_n$=1.62).

The control of gene expression using specific nucleic acid sequences represents a significant step toward preventing or eliminating several genetic diseases, viruses, and cancers. Discovery of RNA interference (RNAi) has made it possible to turn off (silence) specific genes by small interfering RNA (siRNA)—19-24 base-paired RNA fragments with 2-nucleotide overhangs at the 3' ends (Elbashir et al., 2001; McCaffrey et al., 2002; both of which are herein incorporated by reference). An increasing number of experiments using siRNA in various biological systems have overwhelmingly demonstrated siRNA's effectiveness and great potential as the next generation of RNA-based therapeutic agents. Although preliminary results suggest that siRNA is a more potent inhibitor of gene expression and is less toxic to cells than other gene silencing agents (e.g., antisense oligodeoxyribonucleic acids (ODNs) (Xu et al., 2003; Miyagishi et al., 2003; Kretschmer-Kazemi and Sczakiel, 2003; Grunweller et al., 2003; Toth et al., 2002) DNAzymes (Yokota et al., 2004; Lee et al., 2002) or ribozymes (Lee et al., 2002)), its delivery to the appropriate tissues and susceptibility to hydrolytic and enzymatic degradation in the bloodstream still pose a significant challenge (Braasch et al., 2003; Dorsett and Tuschl, 2004; Heidenreich, 2004).

One possibility for effective delivery and protection of siRNA in vivo involves stabilization with synthetic polycations or polycation containing block copolymers to form specialized interpolyelectrolyte complexes (IPECs) or block ionomer complexes (BICs), respectively. Such systems employed with other polynucleic acids are well documented and variations of this concept continue to be employed in gene delivery today (Kabanov and Kabanov, 1995; Kabanov et al., 1989; Perales et al., 1994; Wu and Wu, 1987; Izumrudov et al., 1999; Van de Wetering et al., 1999; Kabanov and Kabanov, 1998; Dautzenberg, 2001; Michaels and Miekka, 1961; Alvarez-Lorenzo et al., 2005; Andersson et al., 2004). IPEC systems used in gene therapy are composed of complexed polycations (e.g. poly(vinyl pyridine) or poly(L- lysine)) and polynucleic acids (e.g., DNA or RNA). Strong electrostatic interactions between oppositely charged polyelectrolytes (e.g., polycations and polynucleic acids) allow for "self-assembly," which can substantially hinder or prevent enzymatic degradation of the incorporated polynucleotide in the bloodstream (Kabanov and Kabanov, 1995; Van de Wetering et al., 1999; Kabanov and Kabanov, 1998). The spontaneous formation of these complexes is largely driven by electrostatic interactions between the synthetic polycations and the "backbone" phosphate units of the polynucleotides. Furthermore, an overall gain in entropy due to the liberation of low molecular weight counterions and water during complexation increases the thermodynamic spontaneity of the process (Kabanov and Kabanov, 1998; Dautzenberg, 2001; Michaels and Miekka, 1961; Alvarez-Lorenzo et al., 2005; Andersson et al., 2004). The structural characteristics and solubility of IPECs in aqueous conditions are governed by the polymeric cation/polynucleotide phosphate (N/P) ratio and are maintained by the formation of non-stoichiometric IPECs, where the N/P ratio $\neq 1$. These imbalanced IPECs can form two types of structures: 1) positive IPECs that contain an excess of polycations; and 2) negative IPECS that contain an excess of unoccupied or unpaired phosphates. While the preparation of these two electrosterically-stabilized IPEC systems does eliminate solubility issues observed with stoichiometric IPECs, the negative IPECS are typically not effective transfection agents and positive IPECs, due to their residual cationic nature, are often too interactive with a host of anionically charged small molecules and organelles (Kabanov and Kabanov, 1998). Unfortunately, stoichiometric IPEC systems are not very soluble in water due to their hydrophobic nature and lack of water-soluble stabilizing moieties.

More recently, the synthesis of block ionomer complexes (BICs) has provided a solution to the many solubility issues observed with conventional IPEC-based systems. Typically, BICs are formed by the complexation of a polyanion, such as DNA or RNA, with a block copolymer composed of cationic and neutral-hydrophilic block-segments. Although there are many examples of copolymers used in the formation of BICs, most incorporate poly(ethylene oxide) (PEO) as the neutral-hydrophilic block along with various cationic block types. For example, poly(ethylene oxide)-block-poly(spermine) (Kbanov and Kabanov, 1995), poly(ethylene oxide)-block-poly(L-lysine) (Katayose and Kataoka, 1996; Wolfert et al., 1996; Katayose and Kataoka, 1997), and poly(ethylene oxide)-block-poly(L-lysine-co-L-glycine) (Kabanov et al., 1996) block copolymer systems have each been used in the formation of stable BICs for gene delivery applications. The use of such neutral, hydrophilic blocks with a cationic block in lieu of a linear cationic homopolymer allows for the preparation of well-defined, electro-neutral (i.e. N/P ratio=1) complexes that are water-soluble and have a greater potential for use as effective transfection agents in gene delivery.

Because of its non-immunogenic properties and its well-documented behavior in the body, PHPMA as a neutral block in conjunction with a suitable cationic block offers great potential for improved transfection and retention behavior of the resulting BIC structures over more traditional PEO-based BIC systems. Such application of these polymers therefore renders a new generation of DNA/RNA delivery agents based on vinyl monomers prepared by a facile, controlled radical polymerization technique. Recently, it has been reported that the chemical coating of polyelectrolyte-based DNA-containing nanoparticles with multifunctional and telechelic PHPMA increased their in vivo residence times (Subr et al., 2006; incorporated herein by reference).

There is always a need for effective drug delivery agents that can be prepared through a controlled process.

SUMMARY OF THE INVENTION

The present invention provides novel non-immunogenic, hydrophilic/cationic block copolymers and their synthesis via aqueous reversible addition fragmentation chain transfer (RAFT) polymerization. Also provided are uses of these copolymers as drug delivery vehicles.

In particular, the present invention discloses the complexation of small interfering ribonucleic acid (siRNA) segments with a series of specifically designed block copolymers consisting of the hydrophilic, non-immunogenic monomer N-(2-hydroxypropyl)methacrylamide (HPMA) and the cationic monomer N-[3-(dimethylamino)propyl]methacrylamide (DMAPMA) for gene delivery applications. Specific compositions of poly(HPMA-b-DMAPMA) copolymers were synthesized via RAFT polymerization and characterized using cationic size exclusion chromatography with multi-angle laser light scattering (SEC-MALLS) and $^1$H NMR spectroscopy. The degree of soluble complex formation was determined by centrifugal filtration experiments and quantitated by scintillation counting of $^{32}$P ATP-labeled siRNA to determine complex solubility and to estimate the degree of complexation relative to cationic and neutral block-lengths. Dynamic and static light scattering methods were employed to determine the hydrodynamic radii, molecular weights, and second virial coefficients of the complexes and to demonstrate their unimodal size distributions. In vitro enzymatic degradation studies of selected siRNA/block copolymer complexes were conducted to demonstrate the enhanced stability of the siRNA/poly(HPMA-b-DMAPMA) complex.

The present invention is directed to a hydrophilic/cationic block copolymer comprising a neutral-hydrophilic polymer and a cationic polymer, both of which have well-defined chain-end functionality. One representative example of such a block copolymer comprises N-(2-hydroxypropyl)methacrylamide (HPMA) and N-[3-(dimethylamino)propyl] methacrylamide (DMAPMA). More specifically, this representative example comprises poly(N-(2-hydroxypropyl) methacrylamide) (PHPMA) and poly(N-[3-(dimethylamino) propyl]methacrylamide) (PDMAPMA); PHPMA and PDMAPMA constitute the neutral-hydrophilic polymer and cationic polymer components of the block copolymer, respectively. Even more specifically, the invention relates to the hydrophilic/cationic block copolymers poly(HPMA-b-DMAPMA) and poly(DMAPMA-b-HPMA). Specific examples of poly(HPMA-b-DMAPMA) include poly(HPMA$_{258}$-b-DMAPMA$_{13}$), poly(HPMA$_{258}$-b-DMAPMA$_{23}$) and poly(HPMA$_{70}$-b-DMAPMA$_{24}$).

The present invention is also directed to a method for producing a hydrophilic/cationic block copolymer, wherein the block copolymer comprises PHPMA and PDMAPMA. This method includes preparing PHPMA in the form of PHPMA macroCTA in aqueous media via reversible addition fragmentation chain transfer (RAFT) polymerization using a suitable primary radical source and chain transfer agent (CTA), adding DMAPMA and additional initiator to the PHPMA macroCTA, and performing a block copolymerization reaction. The last step of this method yields copolymer that comprises PHPMA and PDMAPMA. A preferred embodiment of this method produces poly(HPMA-b-DMAPMA) as the hydrophilic/cationic copolymer. More specifically, the preferred embodiment of this method is related to the production of poly(HPMA$_{258}$-b-DMAPMA$_{13}$), poly(HPMA$_{258}$-b-DMAPMA$_{23}$) and poly(HPMA$_{70}$-b-DMAPMA$_{24}$).

Alternatively, the present invention is drawn to a method for producing a hydrophilic/cationic block copolymer comprising PHPMA and PDMAPMA that includes the steps of preparing PDMAPMA in the form of PDMAPMA macroCTA in aqueous media via reversible addition fragmentation chain transfer (RAFT) polymerization using a suitable primary radical source and chain transfer agent (CTA), adding HPMA and additional initiator to the PDMAPMA macroCTA, and performing a block copolymerization reaction. As with the method above, the last step of this method yields copolymer that comprises PHPMA and PDMAPMA. A preferred embodiment of this method produces poly (DMAPMA-b-HPMA) as the hydrophilic/cationic copolymer.

The present invention is further directed to a method for effectively delivering small interfering RNA (siRNA) or small hairpin RNA (shRNA) to a target site in vivo, which comprises preparing complexes that comprise a hydrophilic/cationic block copolymer and the RNA, and administering the complexes to the target site. The block copolymer in complex with the RNA comprises a neutral-hydrophilic polymer and a cationic polymer both having well-defined chain-end functionality. A representative example of the block copolymer comprises PHPMA and PDMAPMA. Poly(HPMA-b-DMAPMA) and poly(DMAPMA-b-HPMA) are examples of such block copolymers. Yet further examples of block copolymers that can be used in this method are poly(HPMA$_{258}$-b-DMAPMA$_{13}$), poly(HPMA$_{258}$-b-DMAPMA$_{23}$) and poly(HPMA$_{70}$-b-DMAPMA$_{24}$).

The present invention is still further directed to a method for protecting siRNA or shRNA from enzymatic degradation by complexing or encapsulating the RNA with a hydrophilic/cationic block copolymer, which comprises a neutral-hydrophilic polymer and a cationic polymer both having well-defined chain-end functionality. A representative example of the block copolymer comprises PHPMA and PDMAPMA. Poly(HPMA-b-DMAPMA) and poly(DMAPMA-b-HPMA) are examples of such block copolymers. Yet further examples of block copolymers that can be used in this method are poly(HPMA$_{258}$-b-DMAPMA$_{13}$), poly(HPMA$_{258}$-b-DMAPMA$_{23}$) and poly(HPMA$_{70}$-b-DMAPMA$_{24}$).

The present invention also is directed to a method protecting a nucleic acid from enzymatic degradation, comprising the step of complexing the nucleic acid with a hydrophilic/cationic block copolymer, which comprises a neutral-hydrophilic polymer and a cationic polymer both having well-defined chain-end functionality. A representative example of the block copolymer comprises PHPMA and PDMAPMA. Poly(HPMA-b-DMAPMA) and poly(DMAPMA-b-HPMA) are examples of such block copolymers. Yet further examples of block copolymers that can be used in this method are poly(HPMA$_{258}$-b-DMAPMA$_{13}$), poly(HPMA$_{258}$-b-DMAPMA$_{23}$) and poly(HPMA$_{70}$-b-DMAPMA$_{24}$). A preferred embodiment of this method is directed to the protection of the following types of nucleic acid: DNA, DNA encoding a protein, DNA encoding an antisense RNA, DNA encoding a ribozyme, DNA encoding an shRNA, RNA, messenger RNA, siRNA, shRNA, microRNA (miRNA), antisense RNA, and ribozyme RNA.

The foregoing and other advantages of the present invention will be apparent to one of ordinary skill in the art, in view of the following detailed description of the preferred embodiments of the present invention, taken in conjunction with the accompanying drawings.

BRIEF DESCRIPTION OF THE DRAWINGS

Features of the present invention as well as a preferred mode of use, further objectives, and advantages thereof, will best be understood by reference to the following detailed description of an illustrative embodiment when read in conjunction with the accompanying drawings wherein.

DETAILED DESCRIPTION OF THE INVENTION

Figure 1:
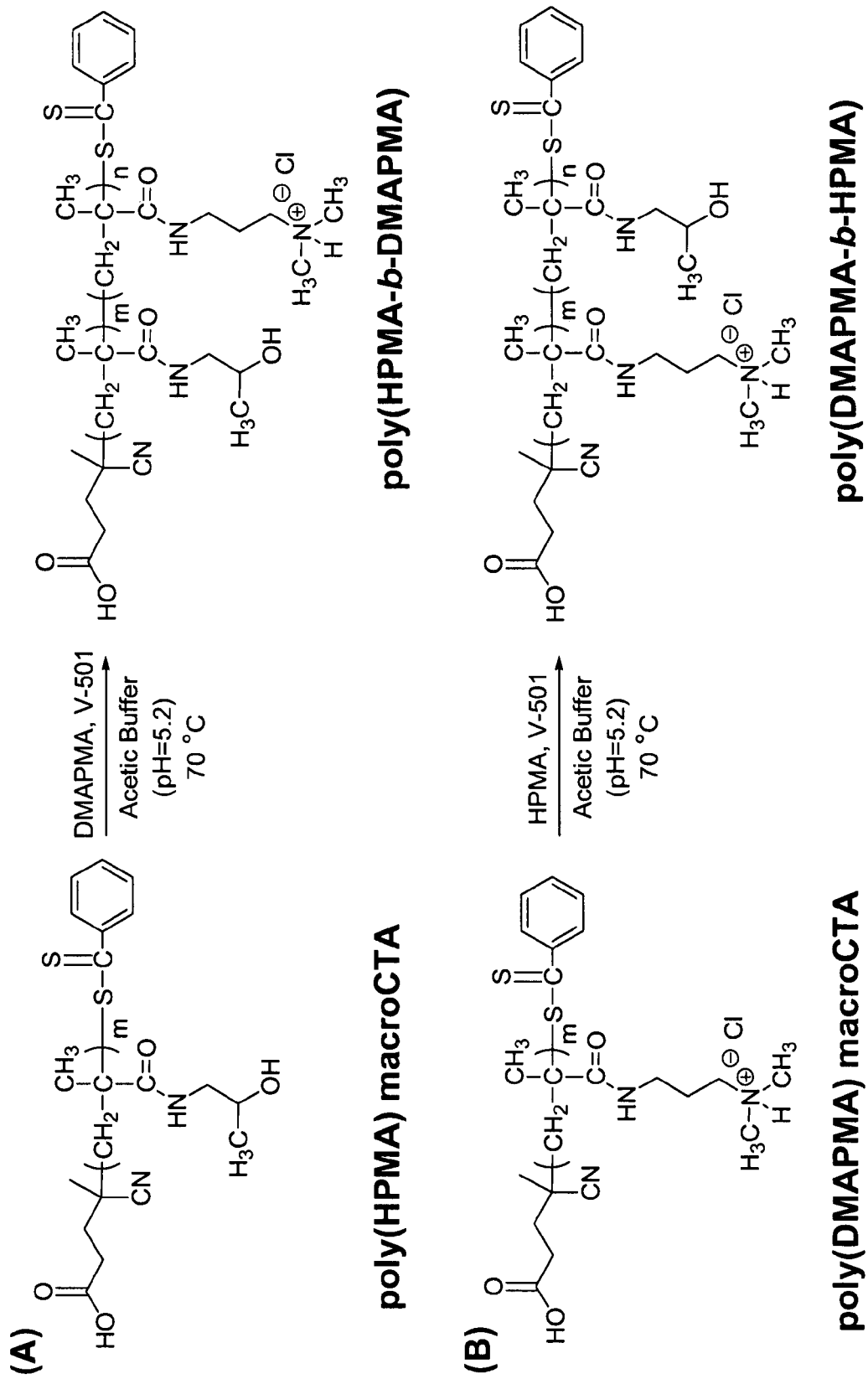
FIG. 1 is a schematic drawing illustrating synthetic pathways for the preparation of HPMA/DMAPMA block-copolymers by aqueous RAFT polymerization at 70° C. under buffered conditions (pH=5.2), (A) chain-extension of poly (HPMA) macroCTA with DMAPMA and (B) chain-extension of poly(DMAPMA) macroCTA with HPMA.

The present invention provides a series of well-defined block copolymers of HPMA and DMAPMA with specific copolymer compositions as well as their preparations. In particular, the synthetic capabilities of the reversible addition fragmentation chain transfer (RAFT) process has been studied in synthesizing novel neutral/cationic block copolymers of N-(2-hydroxypropyl)methacrylamide (HPMA) and cationic methacrylamide, N-[3-(dimethylamino)propyl]methacrylamide (DMAPMA). The preparation of block ionomer complex (BIC) structures by RAFT, containing a collapsed hydrophobic polycation/polyanion core and a PHPMA corona is believed to allow for increased tumor cell uptake and retention of such complexes in the body. Furthermore, RAFT polymerization provides a unique ability to control the length of the neutral and cationic block lengths under aqueous conditions, thus allowing for the tailored synthesis of neutral/cationic blocks that may be used to form well defined BIC-type structures with specific sizes.

An additional advantage of this block copolymer system demonstrated in the present invention is that it has been employed in the formation of BIC-type structures with short interfering RNA (siRNA), a gene silencing agent used in gene "knock-out" experiments. Of the different gene-silencing agents, siRNA is currently the state-of-the-art, boasting higher potency and knock-out specificity than its other counterparts (e.g. antisense deoxyoligonucleotides and ribozymes). Unfortunately, siRNA is quickly destroyed in vivo by common ribonucleases, making it difficult to deliver to specific target cells. The present invention demonstrates successful complexation of HPMA/DMAPMA block copolymers with a 43-nucleotide siRNA that specifically eliminates the production of RNA Polymerase II in human cells. When appropriate HPMA and DMAPMA block lengths are employed for complexation, water-soluble BIC structures are formed. While exhibiting excellent complexation behavior with siRNA, these block copolymer systems also demonstrate a distinct ability to prevent enzymatic degradation of the siRNA by Ribonuclease A (RNase A).

The present invention is directed to a hydrophilic/cationic block copolymer comprising a neutral-hydrophilic polymer and a cationic polymer, both of which have well-defined chain-end functionality. A representative example of such block copolymer comprises N-(2-hydroxypropyl)methacrylamide (HPMA) and N-[3-(dimethylamino)propyl]methacrylamide (DMAPMA) as in poly(HPMA-b-DMAPMA) prepared by chain-extension of poly(HPMA) with DMAPMA or in poly(DMAPMA-b-HPMA) prepared by chain-extension of poly(DMAPMA) with HPMA.

The present invention is also directed to a method for producing a hydrophilic/cationic block copolymer, wherein the block copolymer comprises HPMA and DMAPMA. This method includes preparing poly(N-(2-hydroxypropyl)methacrylamide) (PHPMA) in aqueous media via reversible addition fragmentation chain transfer (RAFT) polymerization using a suitable primary radical source and chain transfer agent, adding DMAPMA to PHPMA, and performing a polymerization reaction. The hydrophilic/cationic block copolymer so produced is poly(HPMA-b-DMAPMA).

Alternatively, a method for producing a hydrophilic/cationic block copolymer comprising HPMA and DMAPMA may include the steps of preparing poly(7V-[3-(dimethylamino)propyl]methacrylamide) (PDMAPMA) in a form of PDMAPMA macroCTA in aqueous media via reversible addition fragmentation chain transfer (RAFT) polymerization using a suitable primary radical source and chain transfer agent (CTA), adding HPMA and additional initiator to PDMAPMA macroCTA, and performing a block copolymerization reaction. The hydrophilic/cationic block copolymer so produced is poly(DMAPMA-b-HPMA).

The present invention is further directed to a method for effectively delivering siRNA or shRNA to a target site in vivo, which comprises preparing complexes having hydrophilic/cationic block copolymer and the RNA, and administering the complexes to the target site. In this method, the block copolymer comprises a neutral-hydrophilic polymer and a cationic polymer that both have well-defined chain-end functionality. A representative example of the block copolymer comprises PHPMA and PDMAPMA. Preferably, both poly(HPMA-b-DMAPMA) and poly(DMAPMA-b-HPMA) are suitable for this method. Still preferably, the target site comprises a neoplasia, such as a cancerous growth (e.g. tumor) that requires therapeutic treatment.

The present invention is still further directed to a method for protecting siRNA or shRNA from enzymatic degradation by complexing or encapsulating the RNA with a hydrophilic/cationic block copolymer, which comprises a neutral-hydrophilic polymer and a cationic polymer both having well-defined chain-end functionality. A representative example of the block copolymer comprises PHPMA and PDMAPMA.

The term "chain-end functionality" is well known in the art and simply refers to functional groups (e.g. amino group, alcohol group) that are present at the termini of extensions branching away from polymer subunits (i.e. monomers). One particular advantage of the compositions and methods of the present invention relates to the preservation of chain-end functional groups during polymer synthesis, which is performed in an aqueous environment. As such, the current invention provides chain-end functionality that is "well-defined" (i.e. unambiguous).

As referred to above, the RAFT process is employed to carry out the present invention. RAFT, which is often called 'living polymerization', is commonly used to prepare block polymers, since the process can be performed in steps; this allows the sequential addition of the appropriate monomer for synthesis of a certain block. The RAFT process is described in WO/1998/001478, which is herein incorporated by reference. Several additional reagents for carrying out RAFT synthetic processes are disclosed in U.S. Pat. Nos. 7,186,786 and 7,179,872, which are herein incorporated by reference.

The nucleic acid/polymer complexes provided by the present invention can be administered in vivo in order to treat a neoplastic site, such as a tumor. Methods of nucleic acid/polymer administration are well known in the art and are described, for example, in U.S. patent application Ser. No. 10/240,877, which is herein incorporated by reference in its entirety. The term "neoplasia" herein refers to any new growth, particularly that growth which may be undesirable. Examples of neoplasia are benign and malignant tumors, as well has dysplasia (pre-cancerous lesions). Non-limiting examples of tumors that can be treated using the present invention are carcinoma, sarcoma, teratoma, leukemia, breast cancer, lung cancer, prostate cancer, colorectal cancer, brain cancer, esophageal cancer, stomach cancer, bladder cancer, pancreatic cancer, cervical cancer, head and neck cancer, ovarian cancer, melanoma, skin cancer, lymphoma, and glioma.

Various nucleic acids are incorporated in the present invention, including DNA, DNA encoding a protein, DNA encoding an antisense RNA, DNA encoding a ribozyme, DNA encoding an shRNA, RNA, messenger RNA, siRNA, shRNA, miRNA, antisense RNA, and ribozyme RNA. Procedures for preparing and handling these different nucleic acids are well known in the art and are disclosed, for example, in U.S. Pat. Nos. 6,712,617 and 7,015,040, both of which are herein incorporated by reference. All these nucleic acids have the common primary structure of polymerized nucleotides, and therefore have a negative 'backbone' provided by phosphate groups. When one or more of these nucleic acids is mixed with the inventive polymer compositions, these phosphate groups partly interact with the positive charges of the PDMAPMA polymer component of the block copolymer; this interaction provides a chemical basis for nucleic acid-polymer complexation as required in the current inventive methods.

The following examples are given for the purpose of illustrating various embodiments of the invention and are not meant to limit the present invention in any fashion.

EXAMPLES

Experimental Design

Materials

All chemicals were purchased from Aldrich at the highest available purity and used as received unless otherwise noted. 4,4'-Azobis(4-cyanopentanoic acid) (V-501, a gift from Wako Pure Chemicals Industries, Ltd.) was recrystallized from methanol. 4-Cyanopentanoic acid dithiobenzoate (CTP) was synthesized according to a procedure in the literature (Mitsukami et al., 2001; incorporated herein by reference). Deionized water (DI $H_2O$) was obtained from a Barnstead NANO-Pure reverse osmosis/filtration unit (resistivity of 18.0 M$\Omega$). Water used in complexation experiments was obtained from Sigma and shown to have no nuclease (DNase or RNase) activity. HPMA was synthesized according to a procedure previously reported (Strohalm and Kopeček, 1978; Kopeček and Bazilova, 1973; both of which are herein incorporated by reference). DMAPMA was purified by vacuum distillation. RNase A was obtained from United States Biological.

Synthesis of poly(HPMA) macroCTA

Poly(HPMA) macroCTA was prepared by aqueous RAFT polymerization employing V-501 as the primary radical source and CTP as the RAFT CTA at 70° C. The polymerization was performed directly in an aqueous acetic buffer (pH=5.2, 0.27 mol/L acetic acid and 0.73 mol/L sodium acetate) with an initial monomer concentration ($[M]_o$) of 1 M in a septa-sealed, round-bottom flask that was purged with nitrogen for 30 minutes prior to polymerization. Two separate macroCTAs were prepared with initial monomer to CTA ratios ($[M]_o/[CTA]_o$) of 200/1 and 800/1, while the CTA to initiator ratio ($[CTA]_o/[I]_o$) for both systems was kept at 5/1. The HPMA macroCTA synthesized with an initial $[M]_o/[CTA]_o$ of 200/1, poly(HPMA$_{70}$), was prepared by dissolving HPMA (11.5 g, 80 mmol), CTP, (112 mg, 0.4 mmol), and V-501 (22.5 mg/0.08 mmol) in a 250 mL round bottomed-flask and diluting the resulting solution to a final volume of 80 mL. The HPMA macroCTA synthesized at an initial $[M]_o/[CTA]_o$ of 800/1, poly(HPMA$_{258}$), was prepared by dissolving HPMA (28.64 g, 200 mmol), CTP (70.0 mg, 0.25 mmol), and V-501 (14.0 mg, 0.05 mmol) in 50 mL buffer (0.272 mol/L acetic acid and 0.728 mol/L sodium acetate, pH=5.3) in a 500 mL round-bottomed flask and diluting the resulting solution to a final volume of 200 mL. Both HPMA macroCTAs ($M_n$=10,000 g/mole, PDI=1.05 and $M_n$=37,000 g/mole, PDI 1.15) were isolated by dialysis in acidic conditions (pH=3-4) at 4° C. followed by lyophilization.

Synthesis of Poly(HPMA-b-DMAPMA) Block Copolymers

As illustrated in FIG. 1(A), block copolymers of HPMA and DMAPMA were prepared directly in aqueous acetic buffer with both HPMA macroCTAs, poly(HPMA$_{70}$) and poly(HPMA$_{258}$), using V-501 as the primary radical source and a $[M]_o$ of 1.0 M DMAPMA. DMAPMA monomer stock solution, pre-neutralized with HCl, was added to each HPMA macroCTA to yield a $[M]_o/[CTA]_o$ of 200/1 and a $[CTA]_o/[I]_o$ of 5/1 for each system.

Chain Extension of Poly(HPMA$_{70}$) with DMAPMA: Block copolymers of poly(HPMA$_{70}$) with DMAPMA were prepared by adding V-501 (22.5 mg, 0.08 mmol), poly (HPMA$_{70}$) (4.0 g, 0.4 mmol), and 63.7 mL of an HCl-neutralized 1.25 mol·L$^{-1}$ DMAPMA stock solution (16.5 g, 80 mmol) to a 100-mL round-bottomed flask. The resulting polymerization solution was divided into four separate 25-mL round-bottomed flasks (i.e. 20 mL per flask) and each flask was subsequently sealed and purged with nitrogen for 30 minutes prior to being submerged in a 70° C. water-bath. Each flask was removed from the water-bath at different time intervals and quenched with liquid nitrogen, yielding copolymers of varying compositions.

Chain Extension of poly(HPMA$_{258}$) with DMAPMA. Block copolymers of poly(HPMA$_{258}$) with DMAPMA were prepared by adding 2 mL of a 7.1 mmol·L$^{-1}$ solution of V-501 (2 mg, 0.0071 mmol), poly(HPMA$_{258}$) (1.85 g, 0.05 mmol), and 8 mL of an HCl-neutralized 1.25 mol·L$^{-1}$ DMAPMA stock solution (2.06 g, 10 mmol) to a scintillation vial. The resulting polymerization solution was divided into five separate 4-mL reaction vials (i.e. 2 mL in each vial) and each vial was subsequently sealed and purged with nitrogen for 30 minutes prior to being immersed in a 70° C. water-bath. The reaction vials were removed from the water-bath at different time intervals and quenched with liquid nitrogen, yielding copolymers of varying compositions.

Synthesis of Poly(DMAPMA) macroCTA

Poly(DMAPMA) was prepared by aqueous RAFT polymerization employing V-501 as the primary radical source and CTP as the RAFT CTA at 70° C. The polymerization was performed directly in an aqueous acetic buffer (pH=5.2, 0.27 mol/L acetic acid and 0.73 mol/L sodium acetate) with a $[M]_o$ of 2 M in a septa-sealed, round-bottom flask that was purged with nitrogen for 30 minutes prior to polymerization. A single poly(DMAPMA) macroCTA was prepared with a $[M]_o/[CTA]_o$ of 294/1 while the $[CTA]_o/[I]_o$ was maintained at 8/1. Generally, DMAPMA (13.62 g, 80.0 mmol) was dissolved in 10 mL of acetic acid/sodium acetate buffer at 0° C., and the pH of the solution was adjusted to 5 with HCl. CTP (76.0 mg, 0.272 mmol) and initiator (9.5 mg, 0.034 mmol) were added and the resulting solution was diluted to 40 mL with additional buffer solution. The solution was degassed by purging with nitrogen for 30 minutes and allowed to react at 70° C. Poly(DMAPMA) macroCTA ($M_n$=17,000 g/mole, PDI=1.05) was isolated by dialysis in acidic conditions (pH=3-4) at 4° C. followed by lyophilization.

Synthesis of Poly(DMAPMA-b-HPMA) Block Copolymers

As illustrated in FIG. 1(B), block copolymers of DMAPMA and HPMA were prepared directly in aqueous acetic buffer with poly(DMAPMA) macroCTA ($M_n$=17,800 g/mole) using V-501 as the primary radical source and a $[M]_o$ of 1.0 M HPMA. HPMA monomer was added to DMAPMA macroCTA to yield a $[M]_o/[CTA]_o$ of 200/1 with a $[CTA]_o/[I]_o$ of 5/1. Copolymers of DMAPMA and HPMA were prepared by adding 0.5 mL of a 4 mmol·L$^{-1}$ solution of V-501 (0.56, 0.002 mmol), DMAPMA macroCTA (170.0 mg, 0.01 mmol), HPMA (0.286 g, 2.0 mmol), and 1.5 mL buffer to a 4-mL reaction vial. The resulting solution was sealed, purged with nitrogen for 30 minutes, and immersed in a 70° C. water-bath. Following sufficient polymerization time, the solution was removed from the water-bath and quenched in liquid nitrogen. The resulting copolymer was isolated by dialysis against water and subsequent lyophilization.

(Co)Polymer Characterization

Both HPMA macroCTAs were characterized by aqueous size exclusion chromatography (ASEC-MALLS) employing an eluent of 20% acetonitrile/80% 0.05 M $Na_2SO_4$ at a flow rate of 0.5 mL/min at 25° C., Tosoh Biosciences TSK-gel columns (G3000 $PW_{XL}$ (<50,000 g/mol, 200 Å) and G4000 $PW_{XL}$ (2000-300 000 g/mol, 500 Å)) with a Polymer Labs LC 1200 UV/vis, Wyatt Optilab DSP interferometric refractometer, and a Wyatt DAWN-EOS multiangle laser light scattering (MALLS) detector ($\lambda$=690 nm). Block copolymers of HPMA and DMAPMA were analyzed by ASEC using an eluent of 1% acetic acid/0.10 M $Na_2SO_4$ (aq) at a flow rate of 0.3 mL/min at 25° C., SynChropak CATSEC columns (100, 300, and 1000 Å; Eichrom Technologies Inc.), a Polymer Labs LC1200 UV/V is detector, a Knauer K-2301 RI detector ($\lambda$=950 nm), and a Wyatt DAWN-DSP multiangle laser light scattering detector ($\lambda$=633 nm). Conversions in each system were determined by comparing the area of the UV signal at 274 nm corresponding to monomer at $t_o$ the area at $t_x$. Absolute molecular weights and polydispersities were calculated using the Wyatt ASTRA SEC/LS software package. Copolymer compositions were determined with a Varian Mercury$^{PLUS}$ 300 MHz spectrometer with a delay time of 5 seconds. $^1$H NMR was used to determine the copolymer composition of poly(HPMA-b-DMAPMA) by integration of the relative intensities of the methyne-proton resonances at 3.78 ppm (macro-HPMA) and the dimethyl-proton resonances at 2.80 ppm (poly(DMAPMA)).

Preparation of siRNA

A 43-nucleotide siRNA against human RNA Polymerase II A was transcribed in vitro from synthetic DNA oligonucleotides by T7 RNA polymerase according to standard procedure (Coleman et al., 2004; incorporated herein by reference). Two DNA oligonucleotides, CGTAATACGACTCACTATT-AGG (SEQ ID NO:1) and GGAGGAGATGGACAA-CAAGTTTGTAACTTGTTGTCCATCTC-CTAATAGTGAGTCGTATTA (SEQ ID NO:2), were annealed at an equal molar ratio to form a partially double-stranded DNA containing the T7 $\phi$2.5 promoter and the template DNA. Upon transcription, an siRNA in the form of a small hairpin, with the sequence of AGGAGAUGGACAACAAGUUACA AACUUGUUGUCCAUCUCCUCC (SEQ ID NO:3), was produced (the underlined nucleotides form base-pairs). For $^{32}$P-labeled siRNA preparation, 1 μM of [$\alpha$-$^{32}$P] ATP was included in the transcription reaction solution. After transcription, the siRNA was purified by 8% denaturing polyacrylamide gel electrophoresis. siRNA was extracted from the gel and recovered by ethanol precipitation. The concentration of siRNA was determined by its absorbance at 260 nm, using an estimated molar extinction coefficient of 355,000 $M^{-1}.cm^{-1}$.

Preparation of poly(HPMA-B-DMAPMA)/siRNA Complexes

Figure 2:
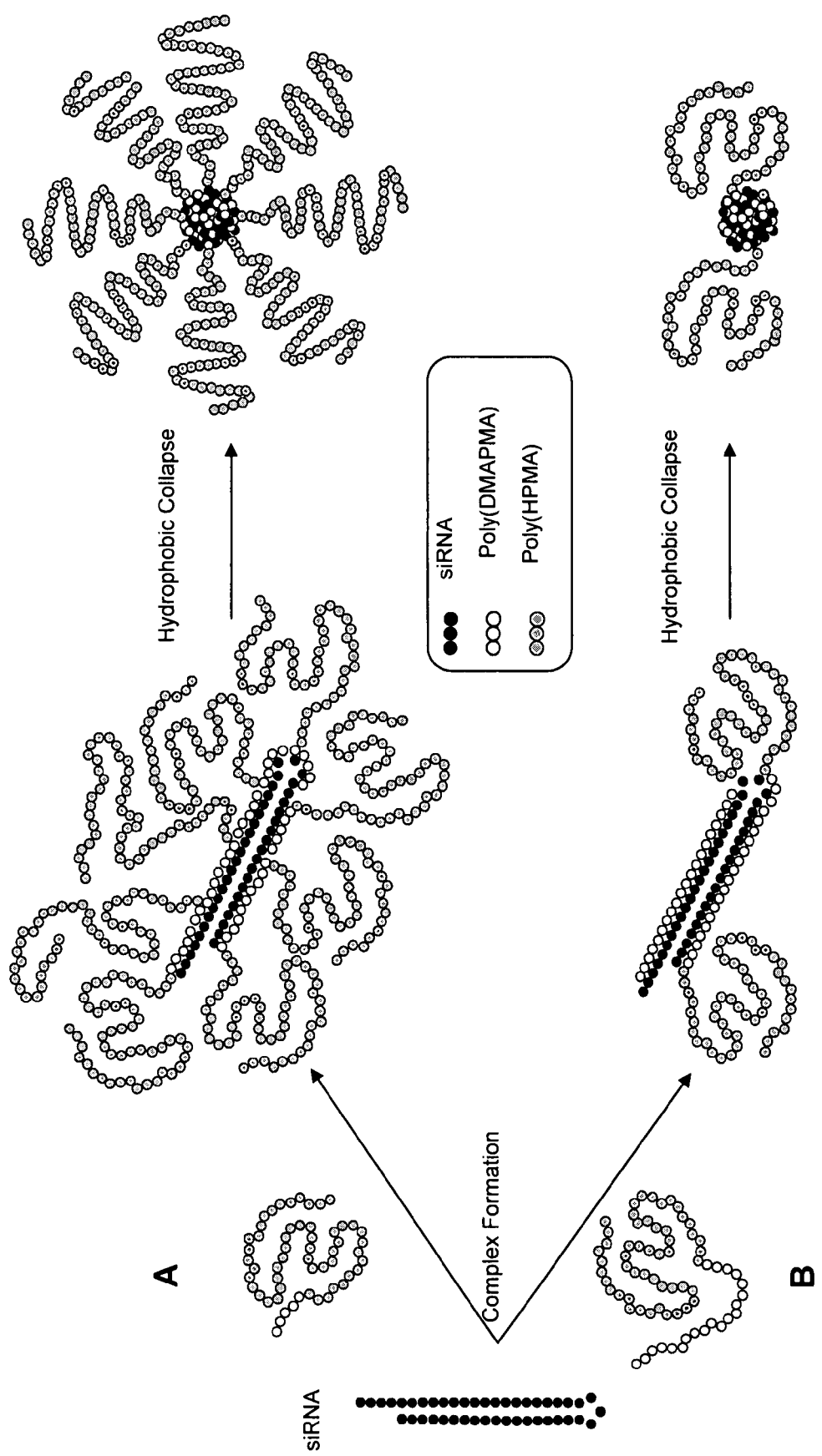
FIG. 2 is a schematic drawing illustrating an idealized representation of the complexation of HPMA/DMAPMA block copolymers with siRNA at (A) short and (B) long DMAPMA block-lengths.

All poly(HPMA-b-DMAPMA)/siRNA complexes were prepared at N/P ratios of 1.0 at 25° C. In a typical preparation, 4 μL of 1 μM $^{32}$P ATP-labeled siRNA (4 pmoles) were added to 10 μL of phosphate-buffered saline solution (pH=7.2, [NaCl]=0.1 M) in a micro-centrifuge tube. The resulting solution was further diluted with appropriate volumes of nuclease free water and (1 μM) block polymer solution to give a final volume of 40 μL and a total siRNA concentration of 50 nM. Complexation solutions were immediately vortexed following addition of polymer solution to allow for homogeneous mixing. FIG. 2 illustrates schematically an idealized complexation of HPMA/DMAPMA block copolymers with siRNA at both short (panel A) and long (panel B) DMAPMA block-lengths.

Centrifugal Filtration Studies of siRNA/Block Copolymer Complexes

Polymer/siRNA complex solutions were characterized by centrifugal filtration studies combined with scintillation counting measurements. In a typical experiment, a 40 μL complex solution was centrifuged at 14,000 RPM for ten minutes to remove any insoluble, precipitated siRNA/block copolymer complexes. The liquid portion of the centrifuged sample was placed in a fresh micro-centrifuge tube and both the dry tube with any precipitated complexes and the solution-filled tube with the remaining siRNA were analyzed by scintillation counting of $^{32}$P ATP-labeled siRNA to obtain the percentages of precipitated and solubilized siRNA, respectively. The centrifuged complex solution was then placed in a siRNA-permeable, Millipore-Microcon YM-50 (regenerated cellulose 50,000 MW cut-off) centrifugal membrane filter and subsequently centrifuged at 14,000 RPM for 3 minutes. The resulting filtrate was analyzed by scintillation counting to quantitate the total amounts of bound/stabilized and unbound siRNA. Theoretical stoichiometric N/P ratios were obtained by preparing and mixing appropriate amounts of 1 μM stock solutions of siRNA and block copolymer. Two separate control experiments, C1 and C2, were employed in order to quantitate the amount of interaction of PHPMA with siRNA and to give a baseline for the amount of siRNA that is able to permeate the 50,000 MW cut-off membrane filter, respectively.

Dynamic Light Scattering (DLS) Experiments

The hydrodynamic diameters ($D_H$) of siRNA/block copolymer complexes were obtained via dynamic light scattering experiments that employed a Malvern-Zetasizer Nano Series DLS detector with a 22-mW He—Ne laser operating at $\lambda$=632.8 nm, an avalanche photodiode detector with high quantum efficiency, and an ALV/LSE-5003 multiple T digital correlator electronics system. Samples were prepared at a total siRNA concentration of 3500 nM and contained a total mass per volume (i.e. block copolymer mass+siRNA mass per mL) of 0.5 mg/mL while maintaining a N/P ratio of 1.0. To remove dust, samples were centrifuged at 14,000 RPM for 10 minutes prior to characterization via DLS. All $D_H$ measurements were performed in triplicate at 25° C. and complex sizes were compared to those of the uncomplexed block copolymers and pure siRNA.

Static Light Scattering (SLS) Experiments

Static light scattering measurements were performed on complexes of siRNA with poly($HPMA_{258}$-b-$DMAPMA_{13}$) using a Malvern Instruments Zetasizer at a constant scattering angle of 173°. The weight-average molecular weight, $M_w$, and second virial coefficient, $A_2$, of selected complexes were determined using the following equation:

$$\frac{K^*c}{R_{\theta=0}} = 2A_2c + \frac{1}{M}$$

where $K^*$, $C_p$, $M_w$, $R^\theta$, and $A_2$ are the optical constant, polymer concentration, molecular weight, Rayleigh ratio, and second virial coefficient, respectively. The specific refractive index increment, dn/dc for the complexes was obtained using the following equation:

$$\left(\frac{dn}{dc}\right)_{Avg.} = w_A\left(\frac{dn}{dc}\right)_A + w_B\left(\frac{dn}{dc}\right)_B + w_C\left(\frac{dn}{dc}\right)_C$$

where $w_A$, $w_B$, and $w_C$ are the mass fractions of the pure polymers PHPMA, PDMAPMA and pure siRNA with dn/dc values of $(dn/dc)_A$, $(dn/dc)_B$, and $(dn/dc)_C$, respectively. Since most of the mass in each complex was composed of PHPMA (i.e. polymer/siRNA=3.3/1), the magnitude of $w_A$ was assumed to be much greater than $w_B$ and $w_C$; therefore, the dn/dc value of 0.168 mL/g for PHPMA in phosphate-buffered saline solution (pH=7.2, [NaCl]=0.1 M) was employed to obtain the $M_w$ for the complexes. LS samples were prepared using an initial stock solution of complexes with a total siRNA concentration of 7200 nM and a total mass per volume (i.e. block copolymer mass+siRNA mass per mL) of 1.0 mg/mL at an N/P ratio of 1.0. To remove dust, samples were centrifuged at 14,000 RPM for 10 minutes. The $R_\theta$ at specific complex concentrations between 1.0 and 0.20 mg/mL were determined by LS and used to construct a Debye plot that yielded the $M_w$ and $A_2$ for the complexes. To prepare different complex concentrations, 20 μL of the 1 mg/mL complex stock solution was placed in a 45-μL LS cuvette and diluted with phosphate-buffered saline using a P2 micro-pipette in 1-2 μL increments. The $R^\theta$ at each concentration was measured to obtain a linear Debye plot.

Enzymatic Degradation Studies of siRNA/Copolymer Complexes

The kinetics of degradation of free and complexed siRNA with RNase A was obtained using a JASCO V-530 spectrophotometer, monitoring at 260 nm (i.e. the $\lambda_{max}$ for RNA) in kinetics/time course mode over a time interval of 25 minutes. Two block copolymer systems were employed in complexation with the siRNA, including poly(HPMA$_{258}$-b-DMAPMA$_{23}$) and poly(HPMA$_{258}$-b-DMAPMA$_{23}$). Complexation was conducted under phosphate-buffered conditions (20 mM, pH=7.4) and employed a total siRNA concentration of 625 nM. As with the centrifugal filtration studies and LS measurements, the polymer stoichiometry was adjusted in each complexation to yield an N/P ratio of 1.0. The kinetics of degradation of siRNA without copolymer stabilization was also determined and employed as a control. In a typical kinetics measurement, 375 pmoles siRNA were combined with 120 μL of phosphate buffer solution (pH=7.4). The resulting solution was further diluted to 600 μL with water and vortexed. 1 μL of block copolymer solution at the appropriate concentration was added to the siRNA solution and the resulting complex solution was immediately vortexed to ensure homogenous mixing. The complex solution was placed in a 1.4 mL quartz cuvette and the initial absorbance at 260 nm ($A_{260}$) was recorded prior to the addition of 2 μL of a 0.35 units/mL RNase A solution. Following rapid mixing, the resulting solution was placed in the spectrophotometer and the $A_{260}$ was monitored over time.

To confirm polymer protection of siRNA against RNase A, analysis of siRNA/polymer complexes by agarose gel electrophoresis was performed. siRNA (1 μg, 70 pmol) in 20 mM phosphate solution (pH 7.4) was mixed with 231 μmol of poly(HPMA$_{258}$-b-DMAPMA$_{13}$) or 187 μmol of poly (HPMA$_{258}$-b-DMAPMA$_{23}$) to maintain an N/P ratio of 1.0. RNase A (0.1 U) was then incubated with the siRNA/polymer complexes for 6 minutes at room temperature in a final volume of 4 μL. Control reactions in the absence of the polymers were also performed. Gel-loading buffer containing 4 μL of 0.2% bromophenol blue, 8 M urea, and 1×TBE buffer (Trisborate-EDTA) was added to the reaction tube. The samples were immediately loaded onto a 1.5% agarose minigel (10 cm×7 cm) and run for 10 minutes at 120 V. After staining with ethidium bromide, the agarose gel was imaged using a CCD camera.

siRNA Release from siRNA/Copolymer Complexes

The demonstration of siRNA dissociation from the siRNA/ polymer complexes was achieved by agarose gel electrophoresis. siRNA/poly(HPMA$_{258}$-b-DMAPMA$_{13}$) complexes (10 μL, containing 1 μg siRNA) in a gel-loading buffer (N/P=1.0, prepared as described above) were loaded at different times onto a 1.5% agarose minigel. The voltage was kept constant at 120 V during electrophoresis. A digital image of the gel was obtained using a CCD camera after ethidium bromide staining.

Results

Synthesis of HPMA/DMAPMA Block (Co)Polymers

Figure 3:
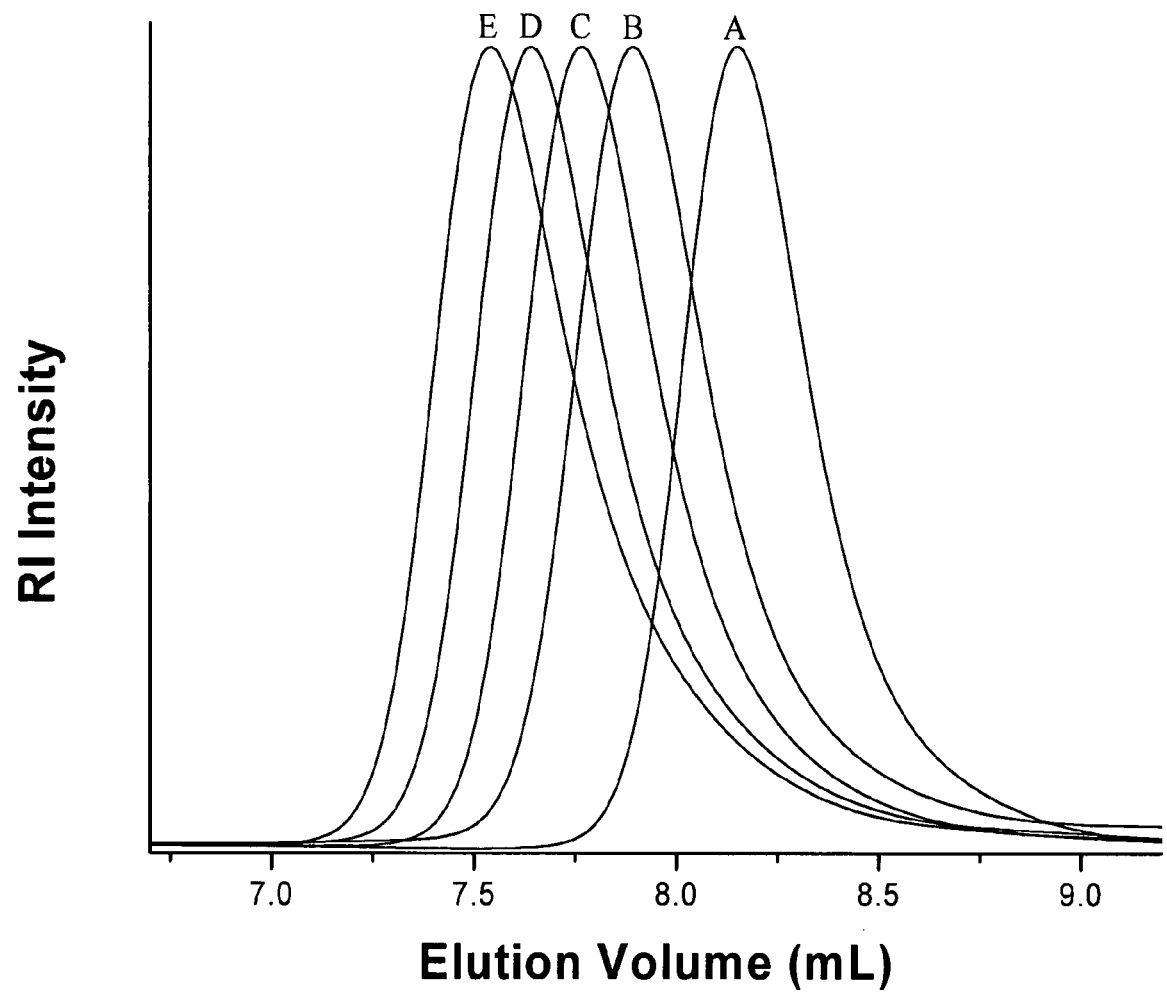
FIG. 3 shows aqueous, cationic SEC-MALLS traces demonstrating the efficient blocking of poly(HPMA$_{70}$) macroCTA with DMAPMA; (A) poly(HPMA) macroCTA, (B) poly(HPMA$_{70}$-b-DMAPMA$_{24}$), (C) poly(HPMA$_{70}$-b-DMAPMA$_{49}$), (D) poly(HPMA$_{70}$-b- and DMAPMA$_{82}$), and (E) poly(HPMA$_{70}$-b-DMAPMA$_{105}$). RI, refractive index.
Figure 4:
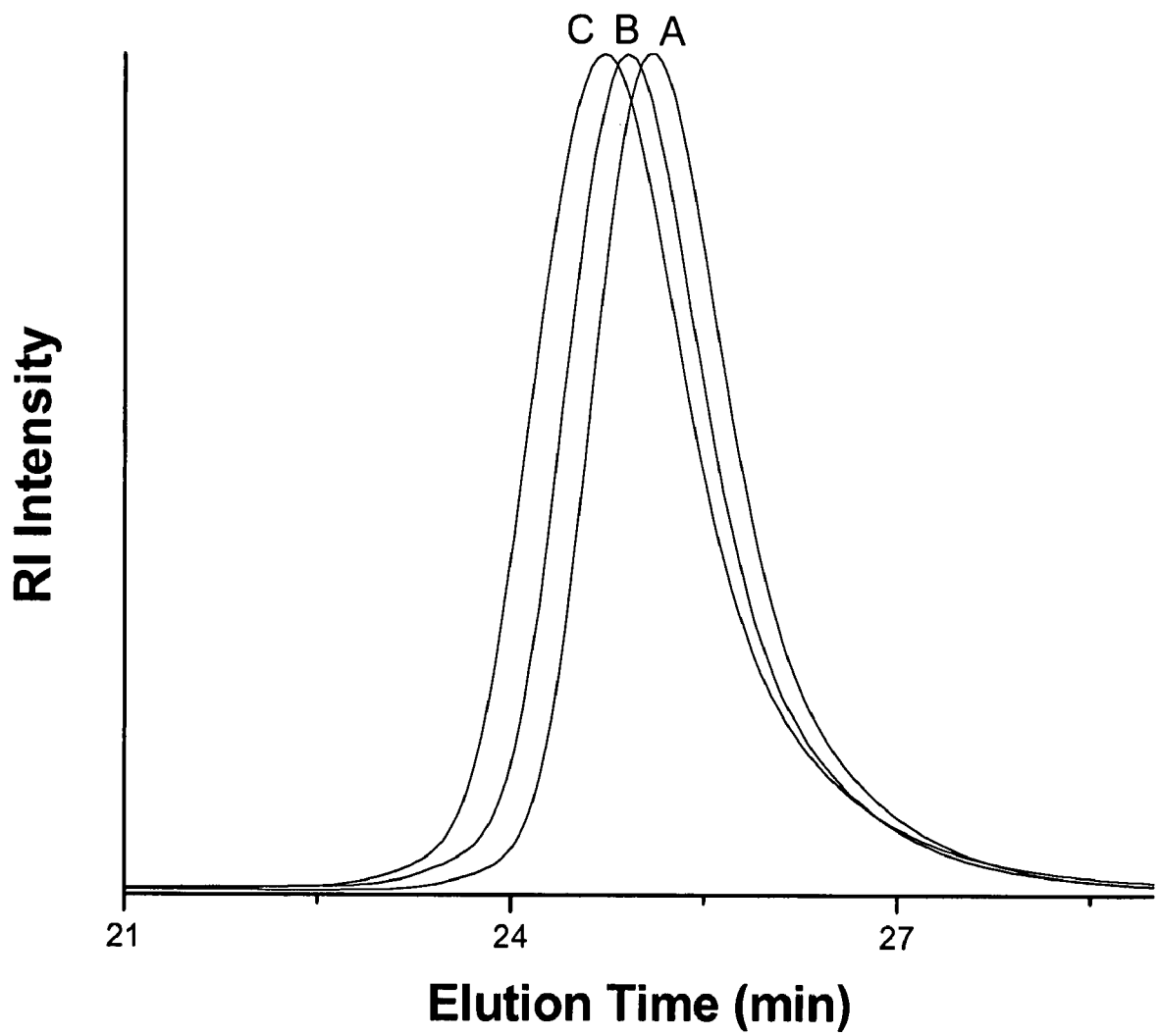
FIG. 4 shows aqueous, cationic SEC-MALLS traces demonstrating the efficient blocking of (A) poly(HPMA$_{258}$) with DMAPMA, resulting in (B) poly(HPMA$_{258}$-b- and DMAPMA$_{23}$) and (C) poly(HPMA$_{258}$-b-DMAPMA$_{53}$). RI, refractive index.

The preparation of block copolymers of HPMA and DMAPMA employed two HPMA macroCTAs, namely poly (HPMA$_{70}$) and poly(HPMA$_{258}$). FIG. 3 shows aqueous, cationic SEC-MALLS traces for the controlled chain-extension of poly(HPMA$_{70}$) with DMAPMA under aqueous conditions at 70° C. via RAFT, while the analogous SEC traces for the controlled chain-extension of poly(HPMA$_{258}$) with DMAPMA is illustrated in FIG. 4. The unimodal nature of the chromatograms coupled with the clear shift to lower elution volumes is qualitatively indicative of high blocking efficiency. Furthermore, Table 1 below lists the conversion, molecular weight, and polydispersity data for each block copolymer system. It is shown that the chain-extensions of both HPMA macroCTAs with DMAPMA proceeded in a controlled fashion, producing block copolymers with low $M_w/M_n$, which is in reasonable agreement between experimental and theoretical molecular weights.

TABLE 1

Conversion, molecular weight, and polydispersity data for the preparation of a series of HPMA and DMAPMA block (co)polymers by aqueous RAFT polymerization

| Copolymer | % Conv.[b] | Composition (Theory) | Composition (exp) | $M_n$ Theory (g/mole) | $M_n{}^a$ (exp) (g/mole) | $M_w/M_n$ |
|---|---|---|---|---|---|---|
| Poly(HPMA$_{70}$-b-DMAPMA$_{24}$) | 12 | 74:26 | 73:27 | 15,000 | 15,400 | 1.08 |
| Poly(HPMA$_{70}$-b-DMAPMA$_{49}$) | 20 | 63:37 | 59:41 | 18,300 | 20,100 | 1.07 |
| Poly(HPMA$_{70}$-b-DMAPMA$_{82}$) | 34 | 51:49 | 46:54 | 24,000 | 27,000 | 1.1 |
| Poly(HPMA$_{70}$-b-DMAPMA$_{105}$) | 45 | 44:56 | 40:60 | 31,100 | 32,000 | 1.11 |
| Poly(HPMA$_{258}$-b-DMAPMA$_{13}$) | 9 | 93:7 | 95:5 | 40,700 | 39,700 | 1.06 |
| Poly(HPMA$_{258}$-b-DMAPMA$_{23}$) | 14 | 90:10 | 92:8 | 42,800 | 41,800 | 1.08 |

TABLE 1-continued

Conversion, molecular weight, and polydispersity data for the preparation of a series of HPMA and DMAPMA block (co)polymers by aqueous RAFT polymerization

| Copolymer | % Conv.[b] | Composition (Theory) | Composition (exp) | $M_n$ Theory (g/mole) | $M_n{}^a$ (exp) (g/mole) | $M_w/M_n$ |
|---|---|---|---|---|---|---|
| Poly(HPMA$_{258}$-b-DMAPMA$_{43}$) | 22 | 15:85 | 86:14 | 46,100 | 45,900 | 1.08 |
| Poly(HPMhd 258-b-DMAPMA$_{53}$) | 25 | 16:84 | 83:17 | 47,300 | 48,000 | 1.11 |
| Poly(DMAPMA$_{77}$-b-HPMA$_{115}$) | 43 | 47:53 | 40:60 | 30,400 | 34,300 | 1.06 |

Figure 5:
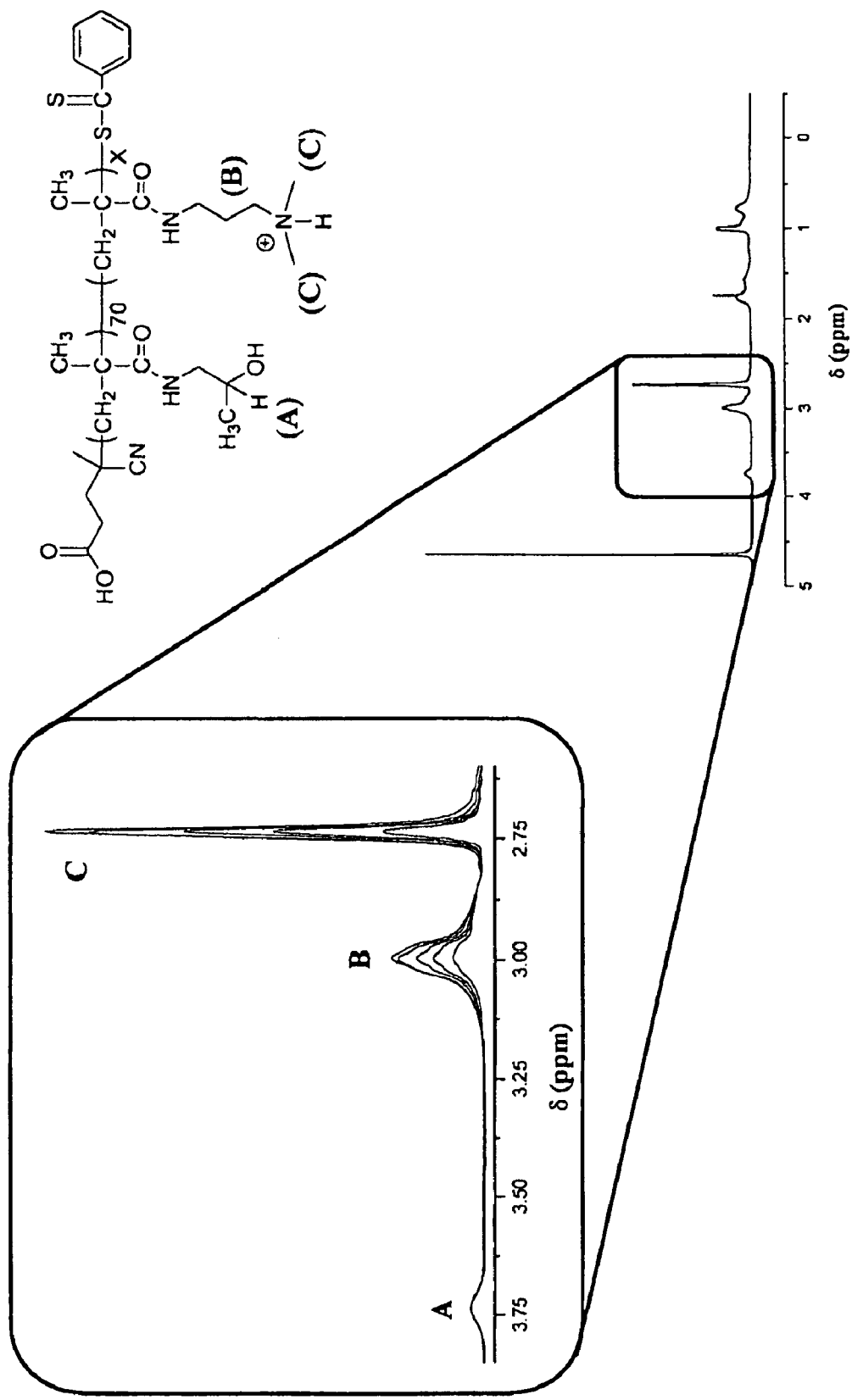
FIG. 5 shows relevant chemical shift assignments for $^1$H NMR spectra of DPMA/DMAPMA block copolymers at different compositions and relevant chemical shift assignments.

[a] AS determined by $^1$H NMR
[b] Conversions were determined by comparison of the UV signal at 274 nm of the monomer at $t_0$ to that at $t_x$ FIG. 5 shows the $^1$H NMR spectra for the series of block copolymers listed in Table 1. Copolymer compositions, and therefore, experimental molecular weights were easily determined by integration of the normalized relative resonances of the methyne-proton peaks at 3.7 ppm (poly(HPMA)) and the dimethyl-proton peaks at 2.7 ppm (poly(DMAPMA)). The copolymer composition data in Table 1 show a small "overshoot" in the experimental molecular weights with respect to theoretical values that can be attributed to the formation of a homopolymer impurity.

Block copolymers of HPMA and DMAPMA were also prepared by chain-extension of poly(DMAPMA$_{77}$) macroCTA with HPMA under aqueous conditions at 70° C.

Figure 6:
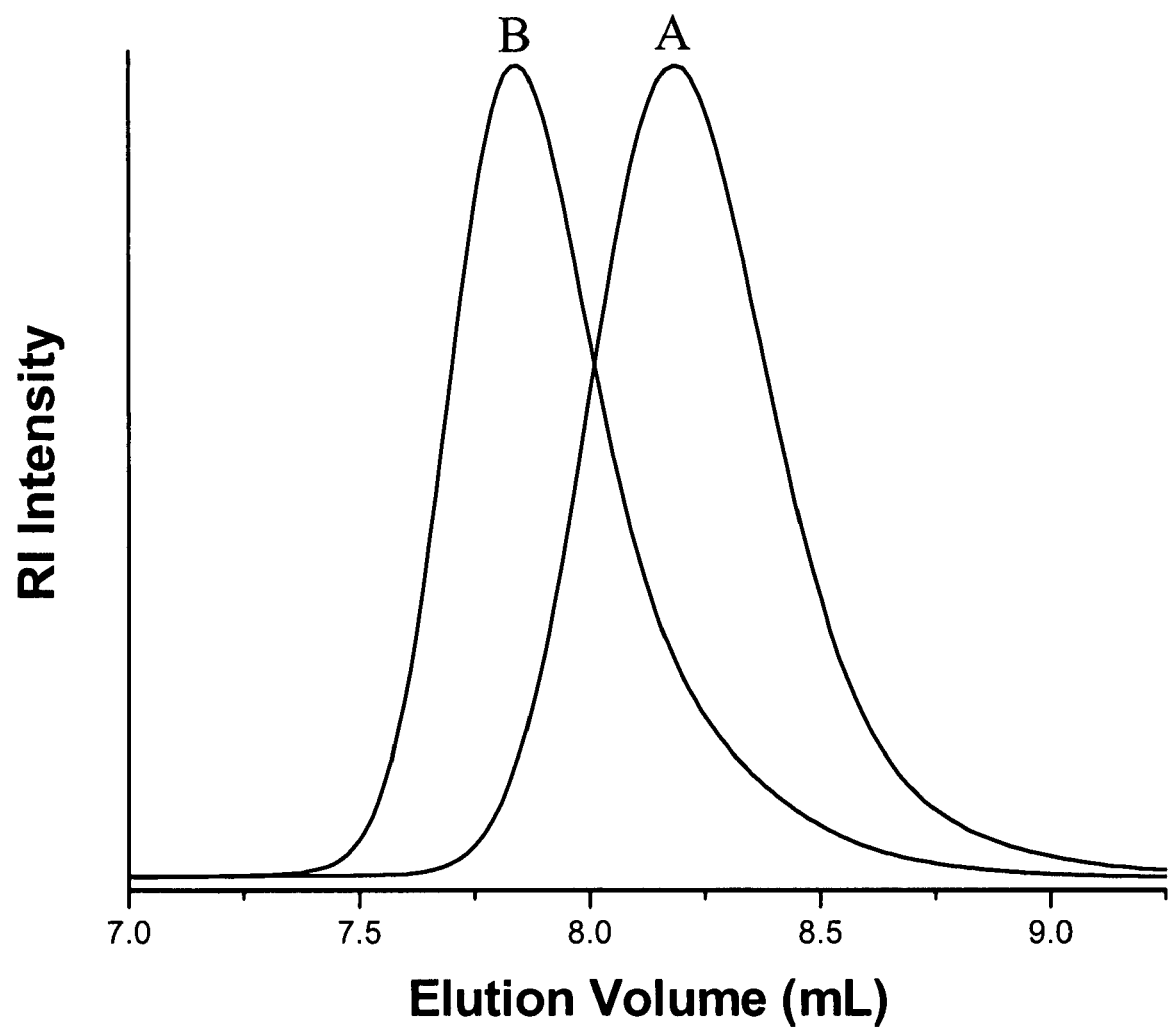
FIG. 6 shows an aqueous, cationic SEC-MALLS chromatogram demonstrating the efficient blocking of DMAPMA macroCTA with HPMA; (A) poly(DMAPMA$_{77}$) macroCTA, and (B) poly(DMAPMA$_{77}$-b-HPMA$_{115}$). RI, refractive index.

FIG. 6 shows the aqueous, cationic SEC traces of poly(DMAPMA$_{77}$) macroCTA and the resulting poly(DMAPMA-b-HPMA) block copolymer. The clear shift of the MWD to lower elution volume with a low amount of "dead" polymer chains being formed is again indicative of efficient blocking and confirms that there is no significant block order dependence when preparing block copolymers of HPMA and DMAPMA via RAFT. As with the chain-extension of HPMA macroCTA with DMAPMA, blocking of DMAPMA macroCTA with HPMA also produces well-defined block copolymers with low $M_w/M_n$ values and reasonable agreement between experimental and theoretical molecular weights.

Synthesis and Characterization of siRNA/Block (Co)Polymer Complexes

The results concerning the complexation of siRNA with RAFT-generated HPMA/DMAPMA (co)polymers (theoretical N/P ratio=1.0) at 25° C. (pH=7.2, 125 mM NaCl, 20 mM phosphate buffer) are listed in Table 2, as monitored by centrifugal filtration studies, are shown in Table 3 and graphically represented in FIG. 7. The general experimental design employed for all complexation reactions is also summarized in Table 2, showing the various block copolymer/siRNA ratios employed to obtain N/P ratios of 1/1 for each system. The control experiments (e.g. entries $C_1$, $C_2$, and $C_3$ in Table 2) behaved as expected, allowing for appropriate comparison between experiments. In the case of C1, poly(HPMA$_{70}$) showed minimal interaction with siRNA. This lack of poly(HPMA)/siRNA interaction is made evident by the fact that nearly 100% of the RNA passes through the centrifugal filter. The second control experiment, C2, consisted of the centrifugal filtration of the siRNA in the absence of any polymer and was conducted in order to account for the portion of siRNA that is retained by adsorption to the centrifugal membrane filter. The quantity of siRNA retained on the filter was reproducible and was therefore used to normalize the other centrifugal filtration experiments, including $C_1$ and $C_3$. The third control experiment, $C_3$, employed poly(DMAPMA$_{77}$) and was used to demonstrate the need for the PHPMA block in the stabilization of siRNA/copolymer complexes.

TABLE 2

Experimental design for complexation of siRNA with poly(HPMA-b-DMAPMA)

| Entry | (Co)Polymer | pMoles RNA | pMoles Polymer | Polymer/RNA Ratio | N/P Ratio |
|---|---|---|---|---|---|
| $C_1$ | poly(HPMA$_{70}$) | 4 | 7 | 1.8 | — |
| $C_2$ | siRNA only | 4 | 0 | 0 | — |
| $C_3$ | Poly(DMAPMA$_{77}$) | 4 | 2.2 | 0.6 | 1 |
| 1 | poly(HPMA$_{70}$-b-DMAPMA$_{24}$) | 4 | 7 | 1.8 | 1 |
| 2 | poly(HPMA$_{70}$-b-DMAPMA$_{49}$) | 4 | 3.5 | 0.9 | 1 |
| 3 | poly(HPMA$_{70}$-b-DMAPMA$_{82}$) | 4 | 2 | 0.5 | 1 |
| 4 | poly(HPMA$_{70}$-b-DMAPMA$_{105}$) | 4 | 1.7 | 0.4 | 1 |
| 5 | poly(HPMA$_{258}$-b-DMAPMA$_{13}$) | 4 | 13 | 3.3 | 1 |
| 6 | poly(HPMA$_{258}$-b-DMAPMA$_{23}$) | 4 | 7.5 | 1.9 | 1 |
| 7 | poly(HPMA$_{258}$-b-DMAPMA$_{43}$) | 4 | 4.0 | 1.0 | 1 |
| 8 | poly(HPMA$_{258}$-b-DMAPMA$_{53}$) | 4 | 3.2 | 0.8 | 1 |

Figure 7:
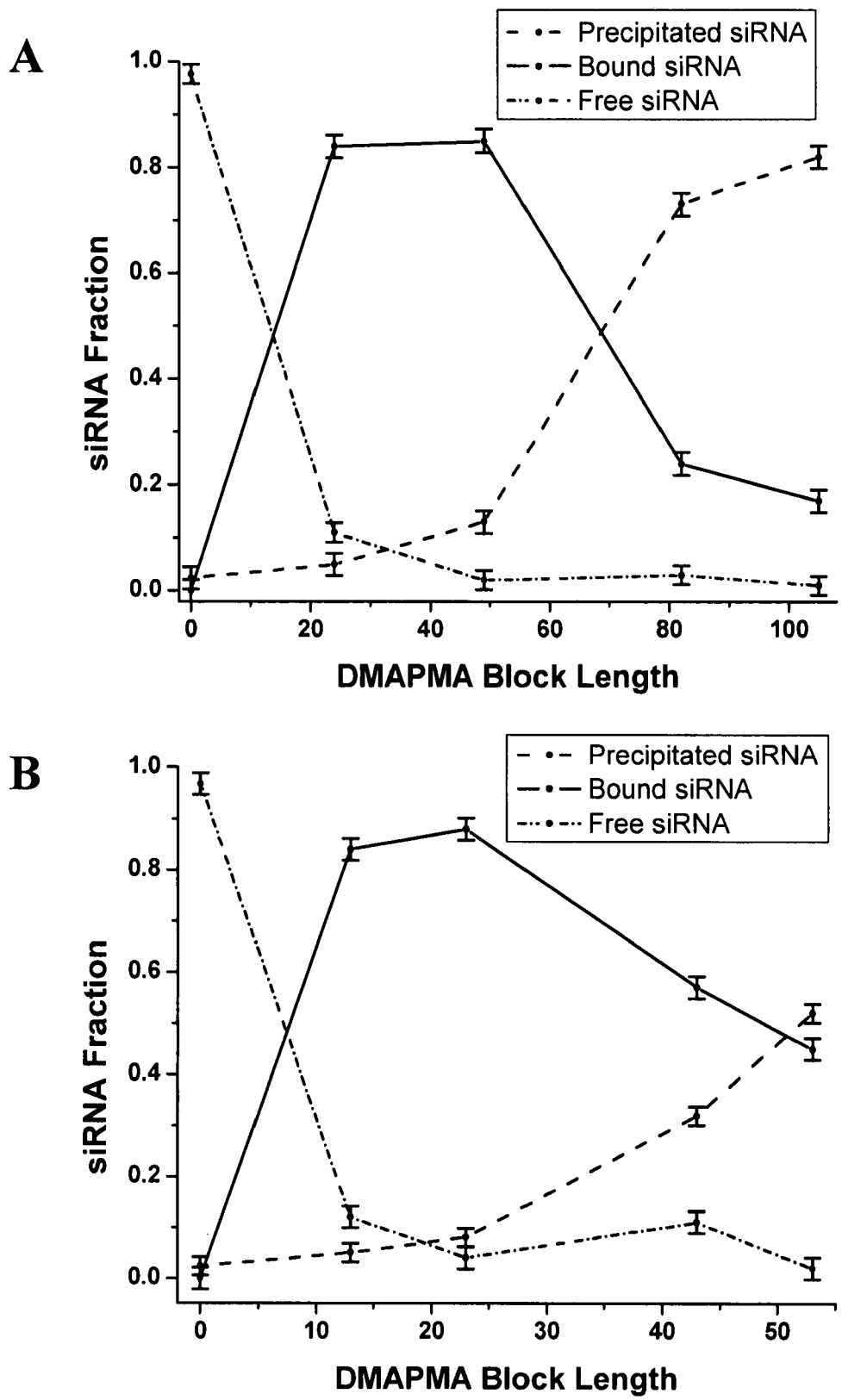
FIG. 7 shows percentages of free, bound/stabilized, and precipitated siRNA following complexation with (A) poly (HPMA$_{70}$-b-DMAPMA$_x$) and (B) poly(HPMA$_{258}$-b-DMAPMA$_x$)copolymers (Theoretical N/P Ratio=1) obtained by scintillation counting as a function of DMAPMA block length.

As illustrated in Table 3 and FIG. 7, the centrifugal filtration experiments show a clear trend between the length of the "complexing" DMAPMA segment and the resulting amounts of solubilized and precipitated siRNA/copolymer complexes. Evidently, copolymers with longer block-lengths of DMAPMA (i.e. poly(HPMA$_{70}$-b-DMAPMA$_{105}$) and poly(HPMA$_{258}$-b-DMAPMA$_{53}$)) lead to higher amounts of complex precipitation and lower amounts of solubilized complexes; whereas, shorter DMAPMA block-lengths (i.e. poly(HPMA$_{70}$-b-DMAPMA$_{24}$) and poly(HPMA$_{258}$-b-DMAPMA$_{13}$)) lead to complexation with minimal participation and higher percentages of solubilized complexes. Since these complexes are prepared to dilute solution, this behavior is thought to be a function of two features dictated by the length of the DMAPMA block: (1) stoichiometric complexes (i.e. complexes with N/P ratios=1.0) prepared with shorter DMAPMA block-lengths contain more hydrophilic HPMA blocks per complex (see FIG. 2(A)) to maintain their solubility than those prepared with longer DMAPMA block-lengths (see FIG. 2(B), and (2) block lengths of DMAPMA that are significantly longer than the length of the siRNA (i.e. DP>>43) cause significant "overhang" of positive and negative charges upon initial complexation, leading to further complexation between individual complexes, ultimately resulting in the formation of insoluble, branched macromolecular aggregates.

TABLE 3

Scintillation counting results for centrifugation and filtration studies following siRNA complexation with poly(HPMA-b-DMAPMA) copolymers (Theoretical N/P ratio = 1)

| Experiment | % Unbound siRNA | % Bound siRNA | % Precipitated siRNA |
|---|---|---|---|
| $C_1$ | 97.6 | 0.0 | 2.4 |
| $C_2$ | 97.0 | 0.0 | 3.0 |
| $C_3$ | 1.0 | 23.0 | 76.0 |
| 1 | 11.0 | 84.0 | 5.0 |
| 2 | 2.0 | 85.0 | 13.0 |
| 3 | 3.0 | 24.0 | 73.0 |
| 4 | 1.0 | 17.0 | 82.0 |
| 5 | 12.0 | 84.0 | 4.0 |
| 6 | 4.0 | 88.0 | 8.0 |
| 7 | 11.0 | 57.0 | 32.0 |
| 8 | 2.0 | 45.0 | 53.0 |

Based on the data presented in FIG. 7, the length of the PHPMA block also appears to affect the stabilization of siRNA/copolymer complexes; however, it plays a lesser role in comparison to the length of the DMAPMA block. Comparison of panel A to panel B implies that there is no advantage gained in using longer PHPMA blocks to form water-soluble siRNA complexes with HPMA/DMAPMA block copolymers. In fact, it suggests that at comparable DMAPMA block-lengths to that of the siRNA, siRNA/copolymer complexes prepared with shorter block-lengths of PHPMA form higher percentages of solubilized complexes than those obtained with longer PHPMA block-lengths. Although this seems counterintuitive, it might be explained in terms of steric effects of the PHPMA block. In particular, assuming DMAPMA block-lengths comparable to that of the siRNA, HPMA/DMAPMA block copolymers containing shorter HPMA block-lengths would be able to bind with the siRNA and pack around a small, hydrophobic core more efficiently and homogeneously than bulkier copolymers prepared with longer PHPMA blocks. This explanation is only speculative and will be further investigated.

Dynamic Light Scattering (DLS) of siRNA/Block (Co)Polymer Complexes

DLS measurements were conducted involving the polymer complex formed with the block copolymer used in entry 5, Table 2, namely poly($HPMA_{258}$-b-$DMAPMA_{13}$). This specific block copolymer system was chosen because of its desirable complexation behavior, i.e. it solubilizes most of the siRNA, with a minimal amount of cationic charge. Theoretically, these properties could prove to be advantageous in future in vivo studies where the ionic interactions in the complexes are sufficiently strong to form complexes and protect the siRNA from enzymatic degradation, but weak enough to release the siRNA at the desired site. Because the concentrations of siRNA employed in the centrifugation studies were too low for accurate DLS measurements, higher concentrations of siRNA were employed (i.e. [siRNA]=3500 nM as opposed to 50 nM). Prior to characterization with DLS, the complexing behavior at higher siRNA concentrations was observed by scintillation counting measurements and found to be identical to that of entry 5 in FIG. 7 (i.e. around 85-90% of the siRNA was complexed and solubilized). The separate hydrodynamic diameters ($D_H$) of poly($HPMA_{258}$-b-$DMAPMA_{13}$), siRNA, and the siRNA/poly($HPMA_{258}$-b-$DMAPMA_{13}$) complex are listed in Table 4. Assuming the formation of multimeric, BIC-based structures and knowing the relative hydrodynamic diameters of the siRNA and poly($HPMA_{258}$-b-$DMAPMA_{13}$) of 3.0 and 9.85, respectively, the $D_H$ value of 11.25 nm obtained for the siRNA/poly($HPMA_{258}$-b-$DMAPMA_{13}$) complex is lower than might be anticipated. However, similar $D_H$ values was recently reported for complexes formed with a comparable 42-nucleotide siRNA and a hydrophobically-modified macrocyclic octamine surfactant (Matsui et al., 2005). The formation of such small complexes slightly greater than 10 nm suggests that the hydrophobic cores within these structures are extremely compact and that larger, more traditional BIC structures composed of multiple copolymer/nucleic acid complexes are not formed in this case. This behavior can be attributed to the fact that the complexation reactions were carried out in extremely dilute conditions, i.e. conditions which prevent the formation of multimeric aggregates during initial complexation.

TABLE 4

Independent hydrodynamic diameters of siRNA, poly($HPMA_{258}$-b-$DMAPMA_{13}$), and the siRNA/poly($HPMA_{258}$-b-$DMAPMA_{13}$) complex obtained by dynamic light scattering

| Sample | Concentration (mg/mL) | $D_H$ (nm) | Standard Deviation (nm) |
|---|---|---|---|
| siRNA | 0.50 | 2.95 | ±0.341 |
| poly($HPMA_{258}$-b-$DMAPMA_{13}$) | 2.00 | 9.84 | ±0.317 |
| siRNA/poly($HPMA_{258}$-b-$DMAPMA_{13}$) Complex | 0.50 | 11.25 | ±0.471 |

Static Light Scattering (SLS) of siRNA/Block (Co)Polymer Complexes

SLS measurements were conducted for the complexes of the block copolymer used in entry 5, Table 2 and in the DLS study above, namely poly($HPMA_{258}$-b-$DMAPMA_{13}$). The compact nature of these BICs is made evident in FIG. 8 by the negative $A_2$ value of $-2.1 \times 10^{-3}$ mL mol/$g^2$ obtained from the slope of the Debye plot. Additionally, the weight-average $M_w$ of siRNA/poly($HPMA_{258}$-b-$DMAPMA_{13}$) complexes was determined by SLS. Because these complexes are prepared with N/P ratios near 1.0, a 3.3/1 poly(HPMA$_{258}$-b-DMAPMA$_{13}$)/siRNA ratio is employed, allowing for a theoretical $M_w$ of 145.2 kDa to be calculated based on the respective molecular weights of the poly(HPMA$_{258}$-b-DMAPMA$_{13}$) and the siRNA. This theoretical $M_w$ was confirmed by SLS which yielded an experimental $M_w$ of 146.7 kDa for complexes of siRNA with poly(HPMA$_{258}$-b-DMAPMA$_{13}$).

Enzymatic Degradation Assay of siRNA/Copolymer Complexes

Figure 9:
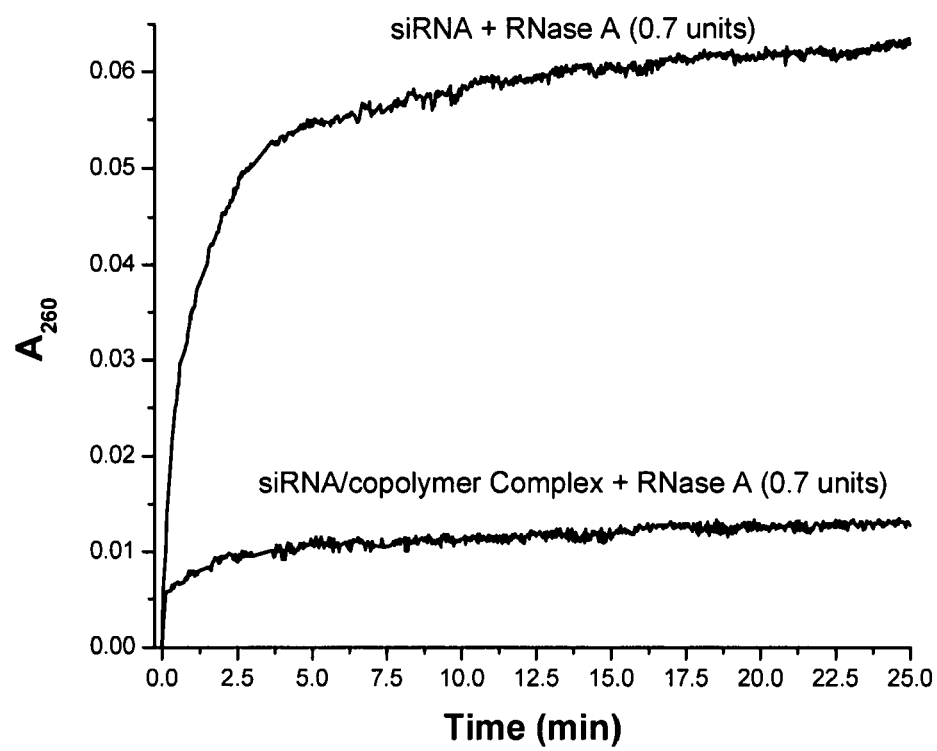
FIG. 9 shows enzymatic degradation of siRNA with RNase A in the presence and absence of (A) poly(HPMA$_{258}$-b-DMAPMA$_{13}$) and (B) poly(HPMA$_{258}$-b-DMAPMA$_{23}$). A$_{260}$, absorbance at 260 nm.
Figure 9:
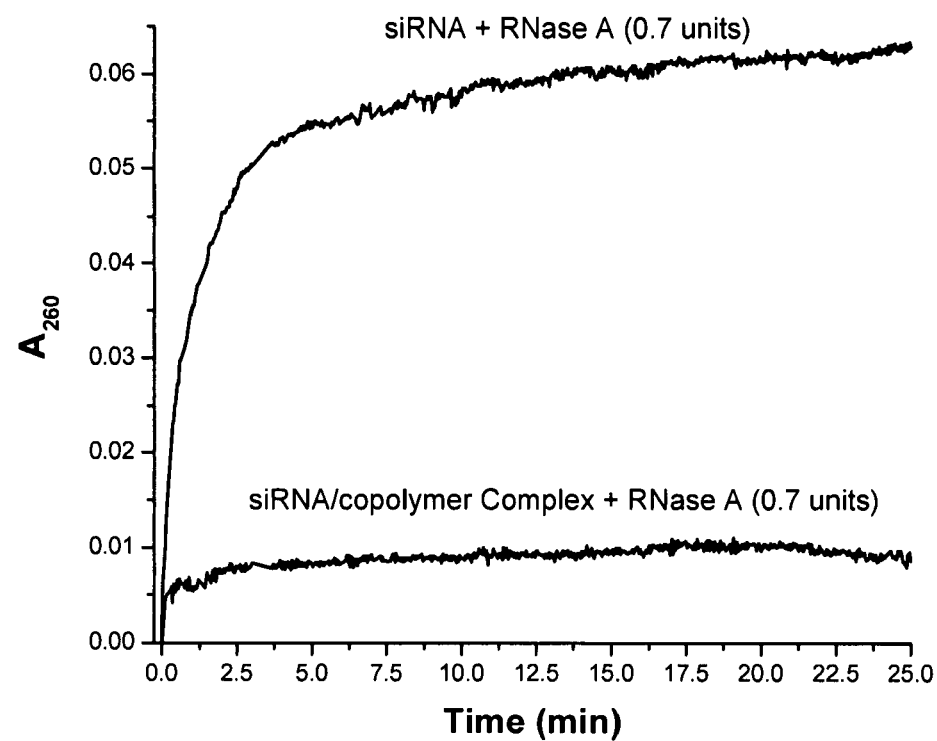
Figure 10:
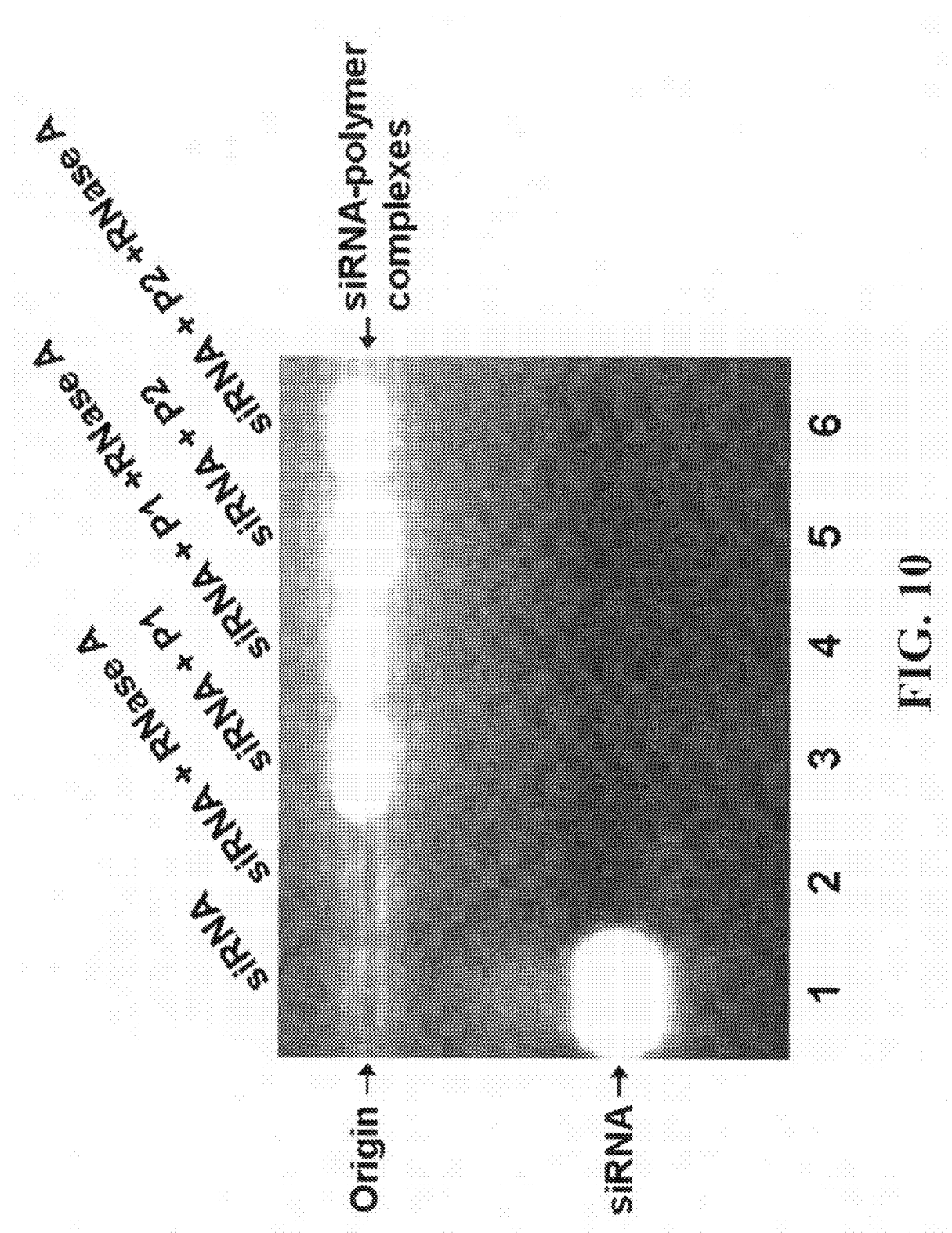
FIG. 10 shows polymer protection of siRNA against RNase A degradation. P1 and P2 represent poly(HPMA$_{258}$-b-DMAPMA$_{13}$) and poly(HPMA$_{258}$-b-DMAPMA$_{23}$), respectively. Each lane has 1 µg siRNA and lanes 2, 4, and 6 contain 0.1 U RNase A. The N/P ratio was kept at 1.0 for lanes 3-6.
Figure 11:
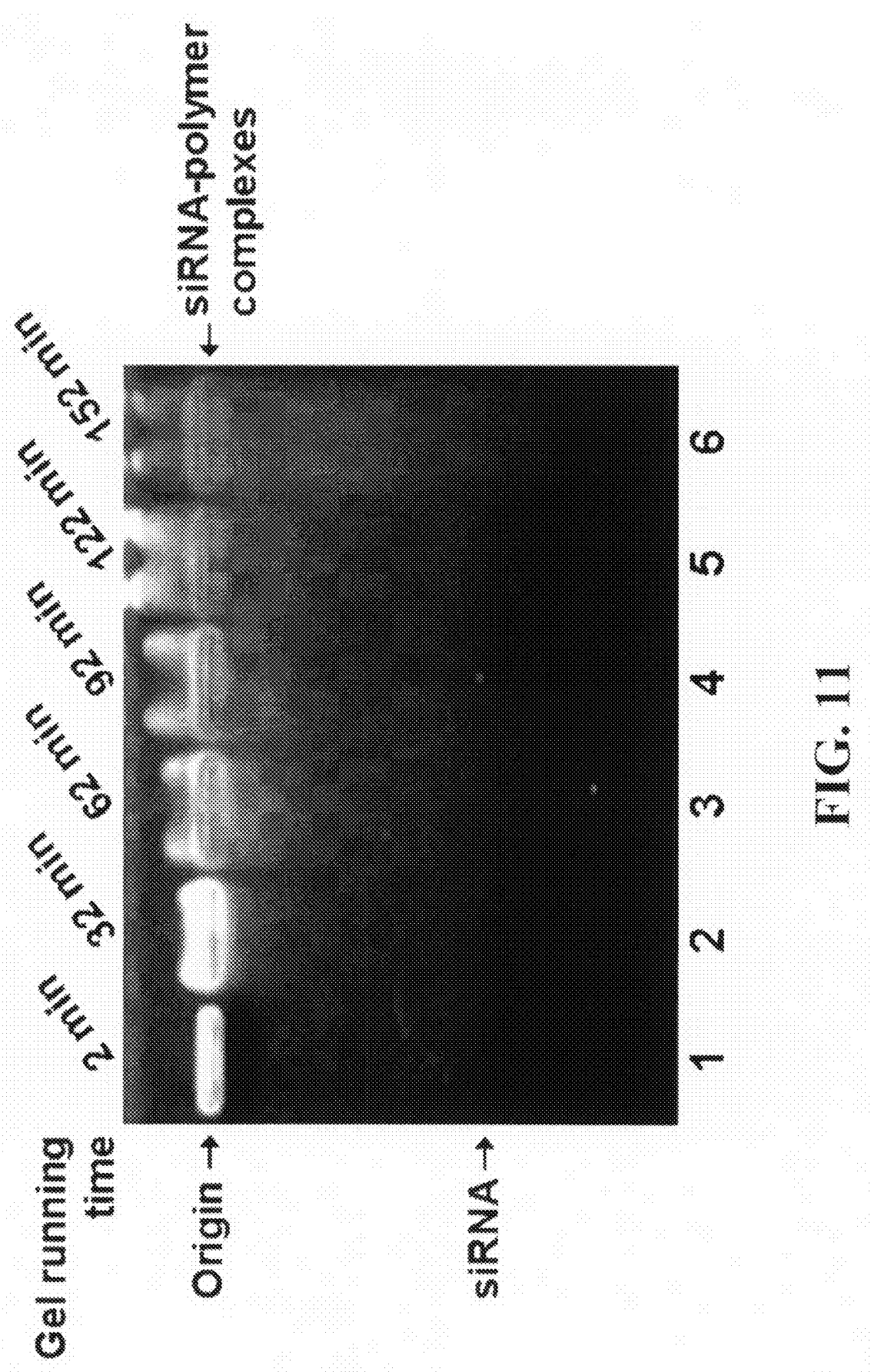
FIG. 11 shows dissociation of siRNA-poly(HPMA$_{258}$-b-DMAPMA$_{13}$) complexes (N/P=1.0) under the conditions of agarose gel electrophoresis. Each lane was loaded at different times with 10 µL siRNA-polymer complexes containing 1 µg siRNA.

The in vitro kinetics of siRNA degradation by RNase A in the presence and absence of HPMA/DMAPMA copolymers was studied in order to evaluate the enhanced stability of siRNA gained by complexation. Two separate block copolymers, poly(HPMA$_{258}$-b-DMAPMA$_{13}$) and poly(HPMA$_{258}$-b-DMAPMA$_{23}$), were chosen for this assay due to their lower cationic content and superior complexation performance, as observed by $^1$H NMR and centrifugal filtration experiments, respectively. FIG. 9 shows conclusive evidence concerning the stabilization of siRNA against enzymatic degradation when protected by HPMA/DMAPMA block ionomers. Since RNase A cleaves at multiple sites on the siRNA, specifically after each cytosine (C) and uracil (U) nucleotide base in the sequence, an increase in $A_{260}$ or hyperchromic effect is observed when the siRNA is degraded (a result of cleavage-induced unfolding of the hairpin as well as subsequent cleavage events of smaller RNA fragments). For both assays, most of the siRNA is consumed in the control experiments (i.e. where free siRNA is combined with RNase A) in less than 5 minutes. However, when siRNA is stabilized with either poly(HPMA$_{258}$-b-DMAPMA$_{13}$) or poly(HPMA$_{258}$-b-DMAPMA$_{23}$) prior to exposure to RNase A, the degradation of siRNA is minimal. For both copolymer systems, there is a small amount of degradation observed initially, which is made evident by a small increase in $A_{260}$ that immediately subsides and levels off, indicating no additional degradation. The initial degradation of siRNA for both complex systems can be attributed to the fact that small amounts of free siRNA are present prior to addition of RNase A. This is supported by the centrifugal filtration studies, where poly(HPMA$_{258}$-b-DMAPMA$_{13}$) and poly(HPMA$_{258}$-b-DMAPMA$_{23}$) both yield small amounts of free siRNA, approximately 12% and 4%, respectively (see Table 3). Furthermore, comparison of the degradation curves between the two polymers shows a lower amount of siRNA degradation for the poly(HPMA$_{258}$-b-DMAPMA$_{23}$) complex system, as would be expected based on its lower amount of free siRNA.

The above conclusion was further corroborated by agarose gel electrophoresis. As can be seen from FIG. 7, unprotected siRNA was completely hydrolyzed within 6 minutes by 0.1 U RNase A (lane 2 as compared with lane 1). On the other hand, both poly(HPMA$_{258}$-b-DMAPMA$_{13}$) and poly(HPMA$_{258}$-b-DMAPMA$_{23}$) can effectively protect the siRNA from RNase A degradation (lanes 4 and 6 as compared with lanes 3 and 5). As expected, the neutral siRNA/polymer complexes (N/P=1.0) do not migrate in an electric field, in contrast to naked siRNA (lane 1).

siRNA Dissociation from siRNA/Copolymer Complexes

Figure 8:
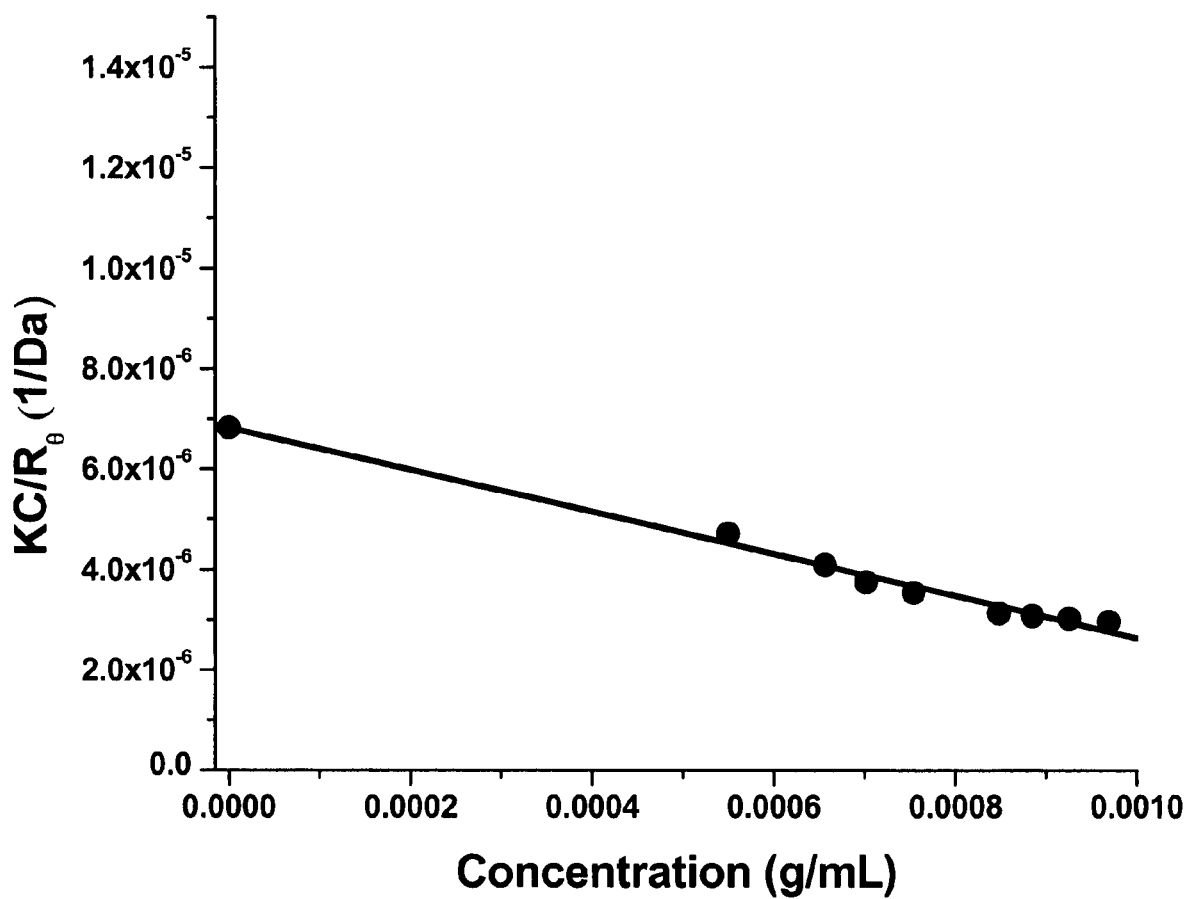
FIG. 8 shows a Debye plot for complexes of siRNA formed with poly(HPMA$_{258}$-b-DMAPMA$_{13}$) and the resulting M$_w$ (weight-average molecular weight) and A$_2$ (second virial coefficient) values. K, Debye constant; C, concentration; R$_\theta$, Rayleigh ratio.

For applications as siRNA stabilization/delivery agents, it is essential that siRNA not only forms stable complexes (for siRNA protection) with the polymers but are also slowly dissociable to make the siRNA available for the formation of an active RNA-induced silencing complex (RISC) that degrades target mRNA. As a preliminary study, gel electrophoresis is particularly suitable for demonstrating siRNA dissociation. Neutral siRNA/polymer complexes (N/P=1.0) do not migrate in an electric field (FIG. 7), but dissociated forms of siRNA possess either positive or negative charges and would migrate toward either the cathode or anode depending on the sign of net charges. FIG. 8 indicates that siRNA is indeed able to dissociate slowly from the siRNA/polymer complexes. As siRNA was slowly released from its complexes during gel electrophoresis, the nonmigrating neutral complexes decreased their intensity at the location of the loading origin (from lane 1 to lane 6, electrophoresed from 2 to 152 minutes). At the same time, dissociated forms of siRNA entered the gel and distributed as a continuous broad band. The migration distance and direction from the origin were dependent upon the time allowed for siRNA dissociation, and the form and effective charge of the respective dissociated siRNA complexes. The gel indicates that slow dissociation of siRNA/polymer complexes can produce both positive and negative siRNA migrating complexes. As expected, a longer gel-running time led to a broader band of siRNA distribution.

CONCLUSIONS AND DISCUSSION

The present study discloses a series of well-defined, near-monodispersed, HPMA/DMAPMA block copolymers and their preparations via aqueous RAFT polymerization in acetic buffer at 70° C. The formation of homopolymer impurity observed in the extension of both HPMA macroCTAs with DMAPMA was minimal and was commonly observed to a low degree in many well-established, RAFT-based, chain-extension experiments using dithioester-based macro-CTAs. The chain-extension of DMAPMA macroCTA with HPMA was also controlled and produced block copolymers with low polydispersities and minimal homopolymer impurity. Further optimization of the chain-extension of HPMA macroCTA with DMAPMA to minimize the formation of homopolymer is currently underway. The ability to prepare block copolymers of HPMA and DMAPMA in either blocking direction demonstrates the synthetic utility of RAFT polymerization for producing block copolymers for the preparation of block ionomer complexes for gene delivery applications.

HPMA/DMAPMA block copolymers were employed in the complexation and ultimate solution stabilization of a 43-nucleotide siRNA under near-physiological conditions. These specific siRNA segments, when appropriately delivered directly to a target-cancer cell, would likely silence the gene that codes for the synthesis of human RNA Polymerase II A (an essential subunit for RNA polymerase II that is responsible for the biosynthesis of all messenger-RNAs in every cell). Studies probing the binding affinity and stabilization effects of these copolymers with siRNA as a function of "complexing" DMAPMA and "stabilizing" HPMA block-lengths suggest that as the length of the DMAPMA block increases, the solubility of the resulting complex decreases. This effect is attributed to two factors relating to the length of the DMAPMA block: (1) shorter DMAPMA block-lengths allow for an increased number of HPMA-blocks to aid in maintaining complex solubility, and (2) longer DMAPMA block-lengths cause significant "charge overhang" of poly (phosphates) (e.g. siRNA) and polyamines (e.g. DMAPMA) which results in an increased occurrence of complex precipitation. Although the number of "stabilizing" HPMA blocks does affect complex stability, the length of the "stabilizing" HPMA block has a lower impact on the stability of the complexes. Further investigations are underway to better understand this experimental observation. In addition, the length of the HPMA block may affect in vivo circulation times, resistance to enzymatic degradation, and tumor cell transfection.

The length of the DMAPMA block has the greatest impact on the stability of the complexes formed; although, the solubilizing effects observed by the HPMA blocks should not be ignored. From an empirical standpoint, longer DMAPMA block-lengths tend to cause an increased amount of precipitation, especially when the length of the complexing DMAPMA block is much greater than that of the siRNA being complexed.

Because of its ability to form soluble siRNA/copolymer complexes, poly(HPMA$_{258}$-b-DMAPMA$_{13}$) was employed at higher concentrations (N/P=1) in dynamic light scattering experiments. A comparison of the relative sizes of the siRNA, block-copolymer, and siRNA/block-copolymer complex revealed that the collapsed complexes are significantly smaller (~11.3 nm) than many of the more conventional PEO-based BIC systems previously reported. The $M_w$ for one of the siRNA/copolymer complexes was determined via SLS and found to be in excellent agreement with the theoretical $M_w$ calculated using a 3.3/1 poly(HPMA$_{258}$-b-DMAPMA$_{13}$)/siRNA ratio. A negative $A_2$ value was also determined for the complexes, indicating that these block ionomer complexes, based on HPMA and DMAPMA, are extremely collapsed, yet seemingly stable in solution.

The ability of these block copolymer systems to protect and stabilize siRNA from enzymatic degradation has also been evaluated by observation of degradation kinetic profiles and comparison to the degradation kinetics of siRNA in the absence of block copolymer. Two HPMA/DMAPMA block copolymer systems that showed promising results in the centrifugal filtration studies were employed, namely poly(HPMA$_{258}$-b-DMAPMA$_{13}$) and poly(HPMA$_{258}$-b-DMAPMA$_{13}$). While exhibiting excellent complexation behavior with siRNA, these block copolymer systems also demonstrated a distinct ability to prevent enzymatic degradation of the siRNA by Ribonuclease A. Further studies using other RNA-degrading enzymes as well as siRNA stabilization in vivo are currently underway.

Studies on modification of HPMA/DMAPMA block copolymer architecture for optimal in vivo release of siRNA (i.e. preparation of poly[HPMA-block-(HPMA-stat-DMAPMA)], attachment of cancer targeting moieties onto the HPMA/DMAPMA block copolymers (i.e. attachment of folate and other receptor-sensitive moieties), and labeling of both siRNA and HPMA/DMAPMA block copolymers with fluorescent tags to allow for in vivo monitoring will also be conducted.

It will be obvious to one of ordinary skill in the art that various modifications may be made without departing from the scope of the invention, which is not to be considered limited to what is described in the specification. All publications cited in the specification are herein incorporated by reference in their entirety.

CITED REFERENCES

Alvarez-Lorenzo, C.; Barreiro-Iglesaias, R.; Concheiro, A.; Iourtchenko, L.; Alakhov, V.; Bromberg, L.; Temchenko, M.; Deshmukh, S.; Hatton, T. A. *Langmuir* 2005, 21, 5142.

Andersson, T.; Aseyev, V.; Tenhu, H. *Biomacromolecules* 2004, 5, 1853.

Braasch, D. A.; Jensen, S.; Liu, Y.; Kaur, K.; Arar, K.; White, M. A.; Corey, D. R. *Biochemistry* 2003, 42, 7967.

Coleman, T. M.; Wang, G.; Huang, F. *Nuc. Acids Res.* 2004, 32, e14.

Dautzenberg, H., In Physical Chemistry of Polyelectrolytes; Radeva, T., Ed.; Marcel Dekker Inc.: New York, 2001; pp 743-792.

Dorsett, Y.; Tuschl, T. *Nature Reviews Drug Discovery* 2004, 3, 318.

Duncan, R. *Chem. Ind.* 1997, 262.

Duncan, R.; Seymour, L. W.; O'Hare, K. B.; Flanagan, P. A.; Wedge, S.; Hume, I. C.; Ulbrich, K.; Strohalm, J.; Subr, V.; Spreafico, F.; Grandi, M.; Ripamonti, M.; Farao, M.; Suarato, M. *J. Controlled Release* 1992, 19, 331.

Elbashir, S. M.; Harborth, J.; Lendeckel, W.; Yalcin, A.; Weber, K.; Tuschl, T. *Nature* 2001, 411, 494.

Godwin, A.; Hartenstein, M.; Müller, A.; Brocchini, S. *Angew. Chem. Int. Ed.* 2001, 40, 594.

Grunweller, A.; Wyszko, E.; Bieber, B.; Jahnel, R.; Erdmann, V. A.; Kurreck, J. *Nuc. Acids Res.* 2003, 31, 3185.

Heidenreich, O. *Curr. Pharm. Biotechnol.* 2004, 5, 349.

Izumrudov, V. A.; Zhiryakova, M. V.; Kudaibergenov, S. E. *Biopolymers* 1999, 52, 94.

Jensen, K. D.; Kopeckova, P.; Bridge, J. B.; Kopecek, J. *J. AAPS PharmSci.* 2001, 4, Article 32.

Jensen, K. D.; Nori, A.; Tijerina, M.; Kopeckova, P.; Kopecek, J. *J. Controlled Release* 2003, 87, 89.

Kabanov, A. V.; Kabanov, V. A. *Adv. Drug Del. Rev.* 1998, 30, 49.

Kabanov, A. V.; Kabanov, V. A. *Bioconjugate Chem.* 1995, 6, 7.

Kabanov, A. V.; Kiselev, V. I.; Chikindas, M. L.; Astafieva, I. V.; Glukhov, A. I.; Gordeev, S. A.; Izumrudov, V. A.; Zezin, A. B.; Levashov, A. V.; Severin, E. S.; Kabanov, V. A. *Dokl. Acad. Nauk. SSSR* 1989, 306, 226.

Kabanov, A. V.; Vinogradov, S.; Suzdaltseva, Y.; Alakhov, V. *Pharm. Res.* 1996, 13, S214.

Katayose, S.; Kataoka, K. *J. Pharm. Sci.* 1997, 87, 160.

Katayose, S.; Kataoka, K., Advanced Biomaterials in Biomedical Engineering and Drug Delivery Systems: Tokyo, 1996.

Kopecek, J.; Bazilova, H. *Eur. Polym. J.* 1973, 9, 7.

Kopecek, J.; Kopeckova, P.; Minko, T.; Lu, Z. R. *Eur. J. Pharm. Biopharm.* 2000, 50, 61.

Kopeckova, P.; Rathi, R. C.; Takada, S.; Rihova, B.; Berenson, M. M.; Kopecek, J. *J. Controlled Release* 1994, 28, 211.

Kretschrner-Kazemi Far, R.; Sczakiel, G. *Nuc. Acids Res.* 2003, 31, 4417.

Lee, N. S.; Dohjima, T.; Bauer, G.; Li, H.; Li, M.-J.; Ehsani, A.; Salvaterra, P.; Rossi, J. *Nature Biotechnol.* 2002, 20, 500.

Matsui, K.; Horiuchi, S.; Sando, S.; Sera, T.; Aoyama, Y. *Bioconjugate Chem.* 2006, 17, 132.

Matsumura, Y.; Maeda, H. *Cancer Res.* 1986, 46, 6387.

McCaffrey, A. P.; Meuse, L.; Pham, T. T.; Conklin, D. S.; Hannon, G. J.; Kay, M. A. *Nature* 2002, 418, 38.

McCormick, C. L.; Lowe, A. B. *Acc. Chem. Res.* 2004, 37, 312.

Michaels, A. S.; Miekka, R. G. *J. Phys. Chem.* 1961, 65, 1765.

Mitsukami, Y.; Donovan, M. S.; Lowe, A. B.; McCormick, C. L. *Macromolecules* 2001, 34, 2248.

Miyagishi, M.; Hayashi, M.; Taira, K. *Antisense Nucleic Acid Drug Delv.* 2003, 13, 1.

Perales, J. C.; Ferkol, T.; Molas, M.; Hanson, R. W. *Eur. J. Biochem.* 1994, 226, 255.

Putnam, D.; Kopecek, J. *J. Adv. Polym. Sci.* 1995, 122, 55.

Rihova, B.; Srogl, J.; Jelinkova, M.; Hovorka, O.; Buresova, M.; Subr, V.; Ulbrich, K. *Ann. N.Y. Acad. Sci.* 1997, 831, 57.

Scales, C. W.; Vasilieva, Y. A.; Convertine, A. J.; Lowe, A. B.; McCormick, C. L. *Biomacromolecules* 2005, 6, 1846-1850.

Strohalm, J.; Kopecek, J. *Angew. Makromol. Chem.* 1978, 109.

Subr, V.; Duncan, R.; Kopecek, J. *J. Biomater. Sci., Polym. Ed.* 1990, 1, 261.

Subr, V.; Konak, C.; Laga, R.; Ulbrich, K. *Biomacromolecules* 2006, 7, 122.

Teodorescu, M.; Matyjaszewski, K. *Macromol. Rapid Commun.* 2000, 21, 190.

Teodorescu, M.; Matyjaszewski, K. *Macromolecules* 1999, 32, 4826.

Toth, J.; Boszormenyi, I.; Majer, Z. S.; Laczko, I.; Malvy, C.; Hollosi, M.; Bertrand, J. R. *Biochem. Biophys. Res. Commun.* 2002, 293, 18.

Van de Wetering, P.; Schuurmans-Nieuwenbroek, N. W. E.; Hennink, W. E.; Storm, G. J. *J. Gene Med.* 1999, 1, 156.

Vasey, P. A.; Kaye, S. B.; Morrison, R.; Twelves, C.; Wilson, P.; Duncan, R.; Thomson, A. H.; Murray, L. S.; Hilditch, T. E.; Murray, T.; Burtles, S.; Fraier, D.; Frigerio, E.; Cassidy, J. *Clinical Cancer Res.* 1999, 5, 83.

Vasilieva, Y. A.; Thomas, D. B.; Scales, C. W.; McCormick, C. L. *Macromolecules* 2004, 37, 2728-2737.

Wang, C.; Stewart, R. J.; Kopecek, J. *Nature* 1999, 397, 417.

Wolfert, M. A.; Schaht, E. H.; Tonceva, V.; Ulbrich, K.; Nazarova, O.; Seymour, L. W. *Human Gene Therapy* 1996, 7, 2123.

Wu, G. Y.; Wu, C. H. *J. Biol. Chem.* 1987, 262, 4429.

Xu, Y.; Zhang, H.; Thormeyer, D.; Larsson, O.; Du, Q.; Elmen, J.; Wahlestedt, C.; Liang, Z. *Biochem. Biophys. Res. Commun.* 2003, 306, 712.

Yeh, P. Y.; Berenson, M. M.; Samowitz, W. S.; Kopeckova, P.; Kopecek, J. *J. Controlled Release* 1995, 36, 109.

Yokota, T.; Miyagishi, M.; Hino, T.; Matsumura, R.; Andrea, T.; Urushitani, M.; Rao, R. V.; Takahashi, R.; Bredesen, D. E.; Taira, K.; Mizusawa, H. *Biochem. Biophys. Res. Commun.* 2004, 314, 283.

---

---

What is claimed is:

1. A hydrophilic/cationic block copolymer comprising a neutral-hydrophilic polymer and a cationic polymer, wherein the neutral-hydrophilic polymer is poly(N-(2-hydroxypropyl)methacrylamide) (PHPMA) and the cationic polymer is poly(N-[3-(dimethylamino)propyl]methacrylamide) (PDMAPMA), and wherein the number of HPMA monomer units range from about 70 to about 258 and the number of DMAPMA monomer units range from about 13 to about 49.

2. The hydrophilic/cationic block copolymer of claim 1, wherein the block copolymer is poly(HPMA-b-DMAPMA) or poly(DMAPMA-b-HPMA).

3. The hydrophilic/cationic block copolymer of claim 2, wherein the block copolymer is poly(HPMA$_{258}$-b-DMAPMA$_{13}$), poly(HPMA$_{258}$-b-DMAPMA$_{23}$) or poly(HPMA$_{70}$-b-DMAPMA$_{24}$).

4. A method for producing a hydrophilic/cationic block copolymer, wherein the block copolymer comprises PHPMA and PDMAPMA, comprising the steps of:

a) preparing PHPMA in aqueous media via reversible addition fragmentation chain transfer (RAFT) polymerization using a suitable primary radical source and chain transfer agent (CTA), wherein the prepared PHPMA is in a form of PHPMA macroCTA;

b) adding DMAPMA and additional initiator to the PHPMA macroCTA; and c) performing a block copolymerization reaction, thereby producing a copolymer according to claim 1 comprising PHPMA and PDMAPMA.

5. The method of claim 4, wherein the hydrophilic/cationic block copolymer is poly(HPMA-b-DMAPMA).

6. A method for producing a hydrophilic/cationic block copolymer, wherein the block copolymer comprises PHPMA and PDMAPMA, comprising the steps of:

a) preparing PDMAPMA in aqueous media via reversible addition fragmentation chain transfer (RAFT) polymerization using a suitable primary radical source and chain transfer agent (CTA), wherein the prepared PDMAPMA is in a form of PDMAPMA macroCTA;

b) adding HPMA and additional initiator to the PDMAPMA macroCTA; and c) performing a block copolymerization reaction, thereby producing a copolymer according to claim 1 comprising PHPMA and PDMAPMA.

7. The method of claim 6, wherein the hydrophilic/cationic block copolymer is poly(DMAPMA-b-HPMA).

8. A method for protecting siRNA, shRNA or miRNA from enzymatic degradation, comprising the step of complexing the siRNA, shRNA or miRNA with a hydrophilic/cationic block copolymer according to claim 1, wherein the block copolymer comprises a neutral-hydrophilic polymer and a cationic polymer both having well-defined chain-end functionality.

9. The method of claim 8, wherein the hydrophilic/cationic block copolymer is poly(HPMA-b-DMAPMA) or poly(DMAPMA-b-HPMA).

10. The method of claim 9, wherein the hydrophilic/cationic block copolymer is poly(HPMA$_{258}$-b-DMAPMA$_{13}$), poly(HPMA$_{258}$-b-DMAPMA$_{23}$) or poly(HPMA$_{70}$-b-DMAPMA$_{24}$).

11. A method for protecting a nucleic acid from enzymatic degradation, comprising the step of complexing the nucleic acid with a hydrophilic/cationic block copolymer according to claim 1, wherein the block copolymer is poly(HPMA-b-DMAPMA) or poly(DMAPMA-b-HPMA).

12. The method of claim 11, wherein the hydrophilic/cationic block copolymer is poly(HPMA$_{258}$-b-DMAPMA$_{13}$), poly(HPMA$_{258}$-b-DMAPMA$_{23}$) or poly(HPMA$_{70}$-b-DMAPMA$_{24}$).

13. The method of claim 11, wherein the nucleic acid is selected from the group consisting of DNA, DNA encoding a protein, DNA encoding an antisense RNA, DNA encoding a ribozyme, DNA encoding an shRNA, RNA, messenger RNA, siRNA, shRNA, miRNA, antisense RNA, and ribozyme RNA.

14. The hydrophilic/cationic block copolymer according to claim 1 further complexed to a nucleic acid.

15. The hydrophilic/cationic block copolymer according to claim 14 wherein the nucleic acid is selected from the group consisting of DNA, DNA encoding a protein, DNA encoding an antisense RNA, DNA encoding a ribozyme, DNA encoding an shRNA, RNA, messenger RNA, siRNA, shRNA, miRNA, antisense RNA, and ribozyme RNA.

* * * * *

SEQUENCE LISTING

```
<160> NUMBER OF SEQ ID NOS: 3

<210> SEQ ID NO 1
<211> LENGTH: 22
<212> TYPE: DNA
<213> ORGANISM: Artificial
<220> FEATURE:
<223> OTHER INFORMATION: Oligonucleotide

<400> SEQUENCE: 1
cgtaatacga ctcactatta gg                                          22

<210> SEQ ID NO 2
<211> LENGTH: 60
<212> TYPE: DNA
<213> ORGANISM: Artificial
<220> FEATURE:
<223> OTHER INFORMATION: Oligonucleotide

<400> SEQUENCE: 2
ggaggagatg gacaacaagt tgtaacttg ttgtccatct cctaatagtg agtcgtatta    60

<210> SEQ ID NO 3
<211> LENGTH: 43
<212> TYPE: RNA
<213> ORGANISM: Artificial
<220> FEATURE:
<223> OTHER INFORMATION: Small hairpin RNA

<400> SEQUENCE: 3
aggagaugga caacaaguua caaacuuguu guccaucucc ucc                   43
```